US012186288B2

(12) United States Patent
Babich et al.

(10) Patent No.: US 12,186,288 B2
(45) **Date of Patent: *Jan. 7, 2025**

(54) DOUBLE TARGETED CONSTRUCTS TO AFFECT TUMOR KILL

(71) Applicant: Cornell University, Ithaca, NY (US)

(72) Inventors: John W. Babich, New York, NY (US); James M. Kelly, Ithaca, NY (US); Alejandro Amor-Coarasa, Ithaca, NY (US); Shashikanth Ponnala, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/906,956

(22) Filed: Jun. 19, 2020

(65) Prior Publication Data

US 2021/0137860 A1 May 13, 2021

Related U.S. Application Data

(63) Continuation of application No. 16/246,422, filed on Jan. 11, 2019, now Pat. No. 10,716,772, which is a continuation of application No. 15/630,808, filed on Jun. 22, 2017, now Pat. No. 10,179,117.

(60) Provisional application No. 62/353,735, filed on Jun. 23, 2016.

(51) Int. Cl.

| | |
|---|---|
| ***C07C 275/16*** | (2006.01) |
| ***A61K 31/17*** | (2006.01) |
| ***A61K 31/19*** | (2006.01) |
| ***A61K 51/04*** | (2006.01) |
| ***A61K 51/10*** | (2006.01) |
| ***C07B 59/00*** | (2006.01) |
| ***C07F 7/22*** | (2006.01) |
| ***G01N 33/574*** | (2006.01) |
| ***G01N 33/58*** | (2006.01) |
| ***G01N 33/60*** | (2006.01) |

(52) U.S. Cl.

CPC .............. *A61K 31/17* (2013.01); *A61K 31/19* (2013.01); *A61K 51/0402* (2013.01); *A61K 51/1072* (2013.01); *C07B 59/001* (2013.01); *C07C 275/16* (2013.01); *C07F 7/2208* (2013.01); *G01N 33/57434* (2013.01); *G01N 33/57492* (2013.01); *G01N 33/58* (2013.01); *G01N 33/60* (2013.01); *C07B 2200/05* (2013.01); *G01N 2500/04* (2013.01)

(58) Field of Classification Search

CPC ............................ C07C 275/16; C07F 7/2208

See application file for complete search history.

(56) References Cited

U.S. PATENT DOCUMENTS

| | | | |
|---|---|---|---|
| 8,211,401 | B2 | 7/2012 | Babich et al. |
| 8,778,305 | B2 | 7/2014 | Pomper et al. |
| 8,921,528 | B2 | 12/2014 | Holt et al. |
| 8,926,944 | B2 | 1/2015 | Babich et al. |
| 9,226,981 | B2 | 1/2016 | Pomper et al. |
| 9,295,739 | B2 | 3/2016 | Schibli et al. |
| 10,806,806 | B2 | 10/2020 | Babich et al. |
| 11,285,227 | B2 | 3/2022 | Babich et al. |
| 11,400,165 | B2 | 8/2022 | Krantz et al. |
| 11,576,986 | B2 | 2/2023 | Salter et al. |
| 2006/0252107 | A1 | 11/2006 | Kubota et al. |
| 2010/0178246 | A1 | 7/2010 | Babich et al. |
| 2015/0064185 | A1 | 3/2015 | Holt et al. |

(Continued)

FOREIGN PATENT DOCUMENTS

| | | |
|---|---|---|
| AU | 2018249559 | 10/2019 |
| CA | 3058663 A1 | 10/2018 |

(Continued)

OTHER PUBLICATIONS

Baccala, et al., "Expression of Prostate-Specific Membrane Antigen in Tumor-Associated Neovasculature of Renal Neoplasms," Urology, 70 (2), 2007, pp. 385-390.

(Continued)

*Primary Examiner* — Shawquia Jackson
(74) *Attorney, Agent, or Firm* — Foley & Lardner LLP

(57) ABSTRACT

The present technology is directed to compounds, compositions, medicaments, and methods related to the treatment of cancers expressing PSMA. The compounds are of Formulas I & II (I)

(II)

(Continued)

or pharmaceutically acceptable salts thereof. The present technology is especially well-suited for use in treating prostate cancer.

2 Claims, 11 Drawing Sheets

(56) References Cited

U.S. PATENT DOCUMENTS

| | | | |
|---|---|---|---|
| 2015/0139905 | A1 | 5/2015 | Chimmanamada et al. |
| 2016/0222036 | A1 | 8/2016 | Babich et al. |
| 2016/0228587 | A1 | 8/2016 | Eder et al. |
| 2017/0070482 | A1 | 3/2017 | Mandyam |
| 2020/0353105 | A1 | 11/2020 | Salter et al. |
| 2021/0121584 | A1 | 4/2021 | Babich et al. |
| 2021/0236667 | A1 | 8/2021 | Fonge et al. |
| 2022/0143228 | A1 | 5/2022 | Ludwig et al. |
| 2022/0143231 | A1 | 5/2022 | Salter et al. |
| 2022/0184217 | A1 | 6/2022 | White et al. |
| 2023/0011134 | A1 | 1/2023 | Salter et al. |
| 2023/0044430 | A1 | 2/2023 | Krantz et al. |
| 2023/0114130 | A1 | 4/2023 | Babich et al. |
| 2023/0122503 | A1 | 4/2023 | Goldberg et al. |

FOREIGN PATENT DOCUMENTS

| | | | |
|---|---|---|---|
| CA | 3070610 | A1 | 7/2021 |
| CN | 110612126 | | 12/2019 |
| EP | 3 609 541 | A1 | 2/2020 |
| JP | 2010-509358 | A | 3/2010 |
| JP | 2011-529919 | A | 12/2011 |
| JP | 2012-511023 | A | 5/2012 |
| JP | 2014-524419 | A | 9/2014 |
| JP | 2014-531407 | A | 11/2014 |
| JP | 2016-535013 | A | 11/2016 |
| JP | 2020-516611 | A | 6/2020 |
| KR | 20190129931 | A | 11/2019 |
| WO | WO 2008/053360 | A2 | 5/2008 |
| WO | WO-2008/058192 | A2 | 5/2008 |
| WO | WO-2010/014933 | A2 | 2/2010 |
| WO | WO-2010/032248 | A2 | 3/2010 |
| WO | WO2015/055318 | A1 | 4/2015 |
| WO | WO-2017/070482 | A2 | 4/2017 |
| WO | WO-2018/187631 | A1 | 10/2018 |
| WO | WO-2022/162210 | A1 | 8/2022 |
| WO | WO-2022/162549 | A2 | 8/2022 |
| WO | WO-2023/026235 | A1 | 3/2023 |
| WO | WO-2023/049963 | A1 | 4/2023 |
| WO | WO-2023/084396 | A1 | 5/2023 |
| WO | WO-2023/084397 | A1 | 5/2023 |

OTHER PUBLICATIONS

Cancer [online], [retrieved on Jul. 6, 2007]. Retrieved from the Internet, URL: http://www.nlm.nih.gov/medlineplus/cancer.html, 10 pages.

Chang, et al., "Five Different Anti-Prostate-specific Membrane Antigen (PSMA) Antibodies Confirm PSMA Expression in Tumor-associated Neovasculature," Cancer Research 59, Jul. 1, 1999, pp. 3192-3198.

Chen, et al., "Quantitative Studies of Allosteric Effects by Biointeraction Chromatography: Analysis of Protein Binding for Low-Solubility Drugs," Analytical Chemistry, vol. 78, No. 8, Apr. 15, 2006, pp. 2672-2683.

Chen, et al., "Radiohalogenated Prostate-Specific Membrane Antigen (PSMA)-Based Ureas as Imagine Agents for Prostate Cancer," J. Med. Chem., 51, 2008, pp. 7933-7943.

Dennis et al., "Imaging Tumors with an Albumin-Binding Fab, a Novel Tumor-Targeting Agent," Cancer Research, vol. 67, Jan. 1, 2007, pp. 254-261.

Fendler, et al., "Preliminary experience with dosimetry, response and patient reported outcome after 177Lu-PSMA-617 therapy for metastatic castration-resistant prostate cancer," Oncotarget, vol. 8, No. 2, 2017, pp. 3581-3590.

Golub, et al., "Molecular Classification of Cancer: Class Discovery and Class Prediction by Gene Expression Monitoring", Science 286: 531-537 (1999).

Haffner, et al., "Prostate-specific membrane antigen expression in the neovasculature of gastric and colorectal cancers," Human Pathology, 40, 2009, pp. 1754-1761.

Hillier et al., "Preclinical Evaluation of Novel Glutamate-Urea-Lysine Analogues That Target Prostate-Specific Membrane Antigen as Molecular Imaging Pharmaceuticals for Prostate Cancer," Cancer Research, vol. 69, pp. 6932-6240, 2009.

International Search Report and Written Opinion on PCT/US2018/026340 (Jul. 27, 2018).

International Search Report and Written Opinion issued on PCT/US2017/038832, mailed Sep. 21, 2017.

Joseph, et al., "The effects of glycation on the binding of human serum albumin to warfarin and L-tryptophan," Journal of Pharmaceutical and Biomedical Analysis, 53, 2010, pp. 811-818.

Kelly et al., "Double Targeting Ligands with Modulated Pharmacokinetics for Endoradiotherapy of Prostate Cancer," J. Nucl. Med, Apr. 27, 2017, 36 pages.

Kelly, et al., "Synthesis and pre-clinical evaluation of a new class of high-affinity 18F-labeled PSMA ligands for detection of prostate cancer by PET imaging," Eur J Nucl Med Mol Imaging, 44, 2017, pp. 647-661.

Kiess et al. "(2S)-2-(3-1Carboxy-5-(4-211AT-Astatobenzamido)Pentyl)Ureido)-Pentanedioc Acid for PSMA-Targeted alpha-Particle Radiopharmaceutical Therapy," J Nucl Med., 2016, vol. 57, pp. 1569-1575.

Kratochwil, et al., "225Ac-PSMA-617 for PSMA-Targeted � FFD3B1-Radiation Therapy of Metastatic Castration-Resistant Prostate Cancer," The Journal of Nuclear Medicine, vol. 57, No. 12, Dec. 2016, pp. 1941-1944.

Kratochwil, et al., "PSMA-Targeted Radionuclide Therapy of Metastatic Castration-Resistant Prostate Cancer with 177Lu-Labeled PSMA-617," The Journal of Nuclear Medicine, vol. 57, No. 8, Aug. 2016, pp. 1170-1176.

Lala, et al., "Role of nitric oxide in tumor progression: Lessons from experimental tumors," Cancer and Metastasis Reviews, (1998), 17(1):91-106.

Maresca, et al., "A Series of Halogenated Heterodimeric Inhibitors of Prostate Specific Membrane Antigen (PSMA) as Radiolabeled Probes for Targeting Prostate Cancer," J. Med. Chem., 52, 2009, pp. 347-367.

Matsuda, "Analysis of Drug-Protein Interactions by High-Performance Affinity Chromatography: Interactions of Sulfonylurea Drugs with Normal and Glycated Human Serum Albumin," Methods in Molecular Biology, vol. 1286, 2015, pp. 255-277.

Non-Final Office Action in U.S. Appl. No. 16/134,789 dated Sep. 20, 2019.

O'Keefe, et al., "Comparative Analysis of Prostate-Specific Membrane Antigen )PSMA) Versus a Prostate-Specific Membrane Antigen-Like Gene," The Prostate 58, 2004, pp. 200-210.

Samplaski, et al., "Folate hydrolase (prostate-specific antigen) 1 expression in bladder cancer subtypes and associated tumor neovasculature," Modern Pathology, 2011, pp. 1521-1529.

Search Report Issued in co-pending European Patent Application No. 17816235, dated Jan. 24, 2020.

Wang, et al., "Expression of Prostate-Specific Membrane Antigen in Lung Cancer Cells and Tumor Neovasculature Endothelial Cells and Its Clinical Significance," PLOS ONE, May 15, 2015, pp. 1-8.

Wernicke, et al., "Prostate-specific Membrane Antigen (PSMA) Expression in the Neovasculature of Gynecological Malignancies: Implications for PSMA-targeted Therapy," Appl Immunohistochem Mol Morphol, vol. 25, No. 4, Apr. 2017, pp. 271-276.

Wustemann, et al., "Protecting salivary glands: Displacement of off-target bound prostate-specific membrane antigen ligands," 2016, p. S15.

(56) References Cited

OTHER PUBLICATIONS

Zechmann, et al., " Radiation dosimetry and first therapy results with a 124I/131 I-labeled small molecule (MIP-1095) targeting PSMA for prostate cancer therapy," Eur J Nucl Med Mol Imaging, 41, 2014, pp. 1280-1292.
Zheng, et al., "Development of enhanced capacity affinity microcolumns by using a hybrid of protein cross-linking/modification and immobilization," Journal of Chromatography A, 1400, 2015, pp. 82-90.
C. Muller et al., "DOTA Conjugate with an Albumin-Binding Entity Enables the First Folic Acid-Targeted 177Lu-Radionuclide Tumor Therapy in Mice", The Journal of Nuclear Medicine, vol. 54, No. 1, pp. 124-131 (Jan. 1, 2013).
Renata Farkas, et al. "64 Cu- and 68 Ga-Based PET Imaging of Folate Receptor-Positive Tumors: Development and Evaluation of an Albumin-Binding N0DAGA-Folate", Molecular Pharmaceutics, vol. 13, No. 6, pp. 1979-1987 (Jun. 6, 2016).
Foreign Search Report on EP 18780348.1 dated Dec. 7, 2020.
Kelly, et al., "Dual-Target Binding Ligands with Modulated Pharmacokinetics for Endoradiotherapy of Prostate Cancer," *The Journ. of Nuclear Medicine*, vol. 58, No. 9, pp. 1442-1449 (Sep. 2017).
Office Action issued in Chinese Patent Application No. 201780046339.7, dated Apr. 23, 2021.
Third Party Submission Under 37 CFR 1.290 on U.S. Appl. No. 17/016,189 dated Jun. 30, 2021 (18 pages).
Third-Party Submission Under 37 CFR 1.290 on U.S. Appl. No. 17/132,552 dated Sep. 29, 2021 (19 pages).
Dvorakova, et al., "Inhibitor-Decorated Polymer Conjugates Targeting Fibroblast Activation Protein," J. of Medicinal Chem., 60(20), pp. 8385-8393 (2017).
Fischer, et al., "Radioimmunotherapy of Fibroblast Activation Protein Positive Tumors by Rapidly Internalizing Antibodies," *Clinical Cancer Research*, 18(22), pp. 6208-6218 (2012).
Huang, et al., "Evaluation of the Tumor Targeting of FAPa-based Doxorubicin Prodrug," *Journal of Drug Targeting*, 19(7), pp. 487-496 (2011).
Non-Final Office Action issued in co-pending U.S. Appl. No. 17/016,189, dated Oct. 21, 2021.
Guo, et al., "Receptor-Targeted Gene Delivery ViaFolate-Conjugated Polyethylenimine," *AAPS Pharmsci.*, 1(4) Article 19, pp. 1-7 (1999).
Non-Final Office Action issued in co-pending U.S. Appl. No. 17/132,552, dated Dec. 13, 2021.
Notice of Reasons for Rejection issued in co-pending Japanese Patent Application No. 2018-567684, dated May 18, 2021.
Siwowska, et al., "Preclinical Comparison of Albumin-Binding Radiofolates: Impact of Linker Entities on the In Vitro and In Vivo Properties," *Molecular Pharmaceutics*, vol. 14, pp. 523-532 (2017).
Notice of Reasons for Rejection issued in co-pending Japanese Patent Application No. 2019-554886, dated Mar. 29, 2022.
Notice of Reasons for Rejection issued in co-pending Japanese Patent Application No. 2018-567684, dated Mar. 29, 2022.
Wang, H. et al., "Bioisosterism of urea-based GCPII inhibitors: Synthesis and structure-activity relationship studies," *Bioorganic & Medicinal Chemistry Letters*, vol. 20(1), pp. 392-397 (2010).
Kumar, A. et al., Design of a Small-Molecule Drug Conjugate for Prostate Cancer Targeted Theranostics, Bioconjugate Chemistry, vol. 27(7), pp. 1681-1689 (2016).
Capello et al., "Peptide Receptor Radionuclide Therapy In Vitro Using [111In-DTPA0] Octreotide", J. Nucl. Med., vol. 44, 2003, pp. 98-104.
Cho et al., "Discovery of a novel fibroblast activation protein (FAP) inhibitor, BR103354, with anti-diabetic and anti-steatotic effects", Scientific Reports, vol. 10, 2020, pp. 1-16.
Dorwald et al., "Side Reactions in Organic Synthesis: A Guide to Successful Synthesis Design", Weinheim: Wiley-VCH Verlag GmbH & Co., 2005, preface.
Dumelin et al., "A Portable Albumin Binder from a DNA-Encoded Chemical Library", Agnew. Chem. Int. Ed., vol. 47, 2008, pp. 3196-3201.
Jackson et al., "Suppression of Tumor Growth in Mice by Rationally Designed Pseudopeptide Inhibitors of Fibroblast Activation Protein and Prolyl Oligopeptidase", Neoplasia, vol. 17, No. 1, 2015, pp. 43-54.
Jansen et al., "Selective Inhibitors of Fibroblast Activation Protein (FAP) with a (4-Quinolinoyl)-glycyl-2-cyanopyrrolidine Scaffold", ACS Med. Chem. Lett., vol. 4, 2013, pp. 491-496.
Non-Final Office Action issued in co-pending U.S. Appl. No. 17/016,189, dated Mar. 13, 2023.
Non-Final Office Action issued in co-pending U.S. Appl. No. 17/132,552, dated Mar. 9, 2023.
O'Dorisio et al., "Characterization of somatostatin receptors on human neuroblastoma tumors", Cell Growth & Differentiation, vol. 5, 1994, pp. 1-8.
Othman et al., "Re-assessing gallium-67 as a therapeutic radionuclide", Nuclear Medicine and Biology, vol. 46, 2017, pp. 12-18.
Shetty et al., "Ga-Labeled Radiopharmaceuticals for Positron Emission Tomography", Nucl. Med. Mol. Imaging, vol. 44, 2010, pp. 233-240.
Tian et al., "Evans Blue Attachment Enhances Somatostatin Receptor Subtype-2 Imaging and Radiotherapy", Theranostics, vol. 8, 2018, pp. 735-745.
Notice of Allowance issued in co-pending U.S. Appl. No. 17/016,189, dated Jul. 12, 2022.
Final Office Action issued in co-pending U.S. Appl. No. 17/132,552, dated Aug. 29, 2022.
Abou, et al., "Towards the stable chelation of radium for biomedical applications with an 18-membered macrocyclic ligand," Chemical Science, vol. 12, pp. 3733-3742 (2021).
Aluicio-Sarduy, et al., "Establishing Radiolanthanum Chemistry for Targeted Nuclear Medicine Applications," Chemistry A European Journal Communication, vol. 26, pp. 1238-1242 (2020).
Bobba, et al., "Influence of short PEG linkers on biodistribution of 225AC-Macropa-YS5, an immunoconjugate for treating CD46 expressing cancer," Abstracts/Nuclear Medicine and Biology, pp. 108-109 (2022).
Macropa-NCS Cat. No. HY-111605, Master of Bioactive Molecules, Aug. 2023, 3 pages.
Randhawa, et al., "Development of novel sulfur-rich ligands for incorporation into mercury-197m/g radiopharmaceuticals," Abstracts/Nuclear Medicine and Biology, pp. 108-109 (2022).
Reissig, et al., "Modulating the pharmacokinetic profile of Actinium-225-labeled macropa-derived radioconjugates by dual targeting of PSMA and albumin," Theranostics, vol. 12, No. 17, pp. 7203-7215 (2022).
Shalgunov, et al., "Radiolabeling of a polypeptide polymer for intratumoral delivery of alpha-particle emitter, 225AC, and beta-particle emitter, 177Lu," Nuclear Medicine and Biology, vol. 104-105, pp. 11-21 (2022).
Thiele, et al., "An Eighteen-Membered Macrocyclic Ligand for Actinium-225 Targeted Alpha Therapy," Angew Chem. Int. Ed. Eng., vol. 56, No. 46, pp. 14712-14717 (2017). [Abstract].
Final Office Action issued in U.S. Appl. No. 17/016,189, dated Dec. 21, 2023.
Final Office Action issued in U.S. Appl. No. 17/132,552, dated Dec. 22, 2023.
Benesova, et al., "Albumin-Binding PSMA Ligands: Optimization of the Tissue Distribution Profile," Mol. Pharmaceutics, vol. 15, pp. 934-946 (2018).
Non-Final Office Action issued in U.S. Appl. No. 17/963,823, dated May 8, 2024.
Non-Final Office Action issued in U.S. Appl. No. 17/700,913, dated Jun. 6, 2024.

DOUBLE TARGETED CONSTRUCTS TO AFFECT TUMOR KILL

CROSS-REFERENCE TO RELATED APPLICATIONS

This application is a continuation of U.S. patent application Ser. No. 16/246,422, filed Jan. 11, 2019, which is a continuation of U.S. patent application Ser. No. 15/630,808, filed Jun. 22, 2017, now U.S. Pat. No. 10,179,117, which claims the benefit of and priority to U.S. Provisional Application No. 62/353,735, filed Jun. 23, 2016, the entire contents of each of which are incorporated herein by reference for any and all purposes.

FIELD

The present technology is directed to compounds, compositions, and methods related to the treatment of tumors that express prostate specific membrane antigen ("PSMA"). The present technology is particulary suited to treat prostate cancer.

SUMMARY

In an aspect, a compound according to Formula I is provided (I)

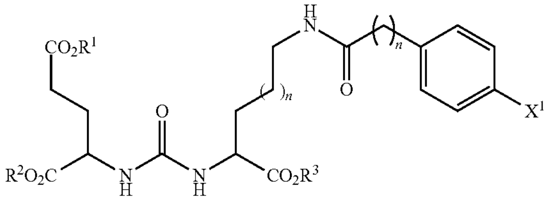

or a pharmaceutically acceptable salt thereof, wherein $X^1$ is $^{124}I$, $^{125}I$, $^{127}I$, $^{131}I$, $^{211}At$, or $Sn(R^4)_3$, $R^1$, $R^2$, and $R^3$ are each independently H, methyl, benzyl, 4-methoxybenzyl, or tert-butyl, $R^4$ is independently at each occurrence an alkyl group; n is 1 or 2; and m is 0, 1, 2, or 3.

In an aspect a compound of Formula II is provided (II)

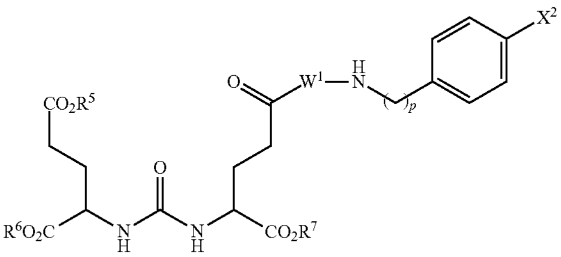

or a pharmaceutically acceptable salt thereof, wherein $X^2$ is $^{124}I$, $^{125}I$, $^{127}I$, $^{131}I$, $^{211}At$, or $Sn(R^8)_3$; $R^5$, $R^6$, and $R^7$ are each independently H, methyl, benzyl, 4-methoxybenzyl, or tert-butyl; $R^8$ is independently at each occurrence an alkyl group; W1 is a bond or —NH-alkylene-; and p is 0, 1, 2, or 3.

In a related aspect, a composition is provided that includes a compound of Formula I or II and a pharmaceutically acceptable carrier.

In a similar aspect, a pharmaceutical composition for treating prostate cancer is provided where the composition includes an effective amount of a compound of Formula I or II.

In an aspect, a method is provided that includes administering a compound of Formula I or II to a subject suffering from prostate cancer.

In an aspect, a method of enhancing uptake of a therapeutic agent to a tumor presenting prostate specific membrane antigen ("PSMA") is provided, where the method includes administering a first therapeutic agent comprising a PMSA targeting moiety and a human serum albumin binding moiety to a subject with one or more prostate cancer tumors, where the human serum albumin binding moiety includes a radionuclide; detecting distribution of the first therapeutic agent in the subject; and modifying the first therapeutic agent to provide a second therapeutic agent.

DESCRIPTION OF THE DRAWINGS

(FIG. 1A) and of a compound of the present technology $^{131}$I-RPS-005 at 24, 48, 72 and 96 h p.i. (FIG. 1B).

DETAILED DESCRIPTION

Figure 1A:
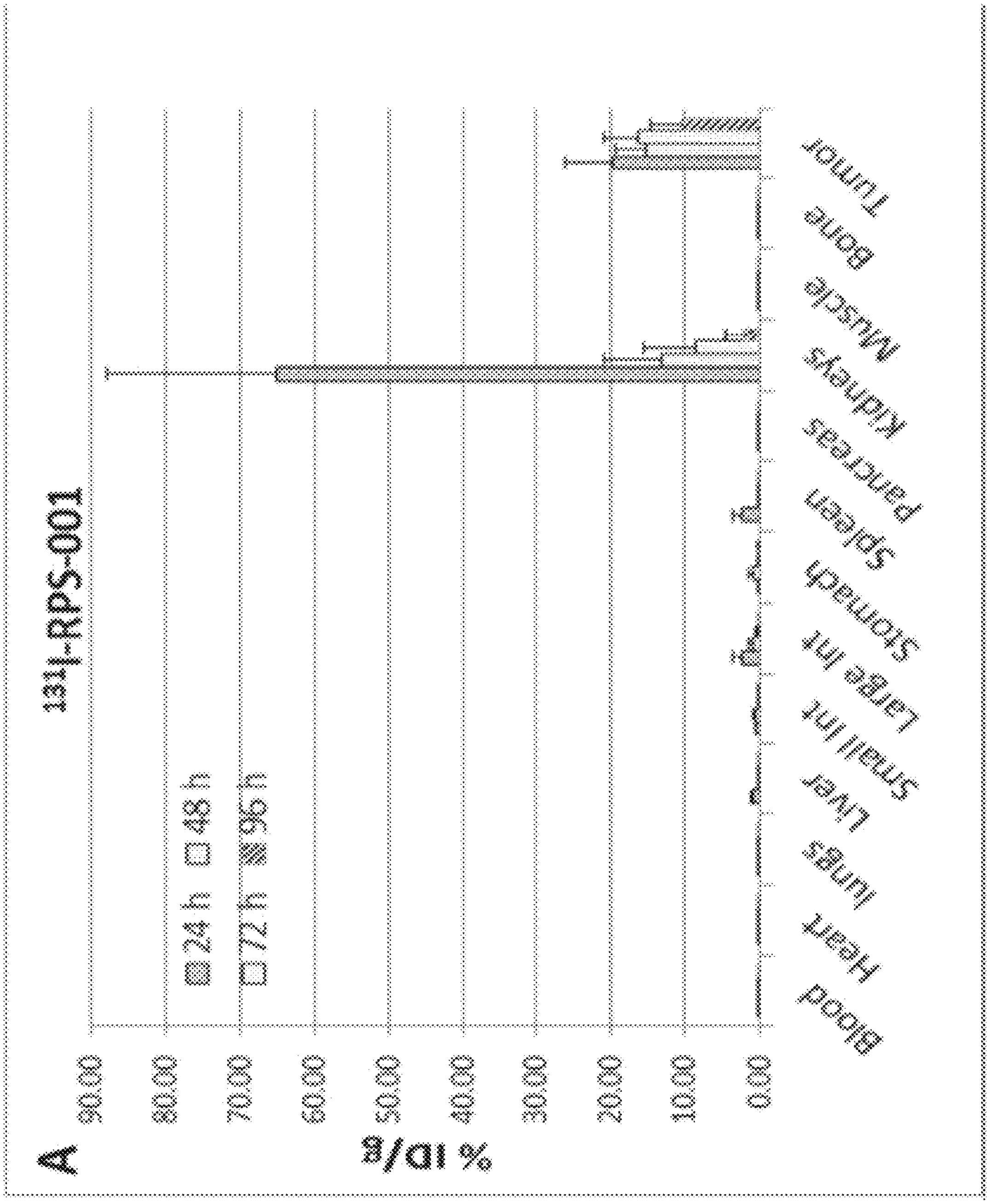
FIGS. 1A-1B provide the biodistribution in male nude mice bearing PSMA+LNCaP human tumor xenografts of $^{131}$I-RPS-001 at 24, 48, 72 and 96 h p.i.

In various aspects, the present, technology provides compounds and methods for treatment of cancer expressing PSMA, and are particulary suited to treat prostate cancer. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Ail methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$, and $^{35}S$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I), hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides, hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡$CCH_3$, —$CH_2C$≡$CCH_3$, —C≡$CCH_2CH(CH_2CH_3)_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups may be substituted or un substituted. Aryl groups herein include monocyclic, bicyclic- and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase “aryl groups” includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or un substituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase “heterocyclyl group” includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl, Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyi, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindoiyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase “heteroaryl groups” includes fused ring compounds. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methy 1, imidazol-4-yl-methyl, pyridin-3-yl-methyl, tetrahydrofuran-2-yl-ethyl, and indol- 2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are aryl ene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of eycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —C(O)OH group. The term "protected carboxylate" refers to —C(O)O-G groups, where G is a carboxylate protecting group, Carboxylate protecting groups are well known to one of ordinary skill in the art. An extensive list of protecting groups for the carboxylate group functionality may be found in Protective Groups in Organic Synthesis, Greene, T. W.; Wuts, P, G. M., John Wiley & Sons, New York, NY, (3rd Edition, 1999) which can be added or removed using the procedures set forth therein and which is hereby incorporated by reference in its entirety and for any and all purposes as if fully set forth herein.

The term "ester" as used herein refers to —$COOR^{70}$. $R^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —$C(O)NR^{71}R^{72}$, and —$NR^{71}C(O)R^{72}$ groups, respectively, $R^{71}$ and $R^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—$C(O)NH_2$) and formamide groups (—NHC(O)H), In some embodiments, the amide is —$NR^{71}C(O)$—($C_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and G-urethane groups, i.e., —$NR^{73}C(O)OR^{74}$ and —$OC(O)NR^{73}R^{74}$ groups, respectively, $R^{73}$ and $R^{74}$ are independently a substituted or unsubstituted alkyl, alkenyl, alkynyl, cycloalkyl, aryl, aralkyl, heterocyclylalkyl, or heterocyclyl group as defined herein. $R^{73}$ may also be H.

The term "amine" (or "amino") as used herein refers to —$NR^{75}R^{76}$ groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethyl amino, diethylamino, propylamino, isopropyl amino, phenylamino, or benzylamino.

The term "sulfonamide" includes S- and N-sulfonamide groups, i.e., —$SO_2NR^{78}R^{79}$ and —$NR^{78}SO_2R^{79}$ groups, respectively. $R^{78}$ and $R^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—$SO_2NH_2$). In some embodiments herein, the sulfonamido is —$NHSO_2$-alkyl and is referred to as the "alkylsulfonylamino" group.

The term "thiol" refers to —SH groups, while "sulfides" include —$SR^{80}$ groups, "sulfoxides" include —$S(O)R^{81}$ groups, "sulfones" include —$SO_2R^{82}$ groups, and "sulfonyls" include —$SO_2OR^{83}$. $R^{80}$, $R^{81}$, $R^{82}$, and $R^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —$NR^{84}$—$C(O)$—$NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —$C(NR^{87})NR^{88}R^{89}$ and —$NR^{87}C(NR^{88})R^{89}$, wherein $R^{87}$, $R^{88}$, and $R^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to $NR^{90}C(NR^{91})NR^{92}R^{93}$, wherein $R^{90}$, $R^{91}$, $R^{92}$ and $R^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —$C(R^{94})$═$C(R^{95})NR^{96}R^{97}$ and —$NR^{94}C(R^{95})$═$C(R^{96})R^{97}$, wherein $R^{94}$, $R^{95}$, $R^{96}$ and $R^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —$O^-$. A "hydroxyalkyl" group is a hydroxyl-substituted alkyl group, such as HO—$CH_2$—.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art ail language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, trifluoroacetic acid, benzoic acid, gluconic acid, fumaric-acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanol amine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

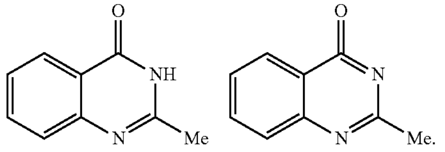

As another example, guanidines may exhibit the following isomeric forms in protic organic solution, also referred to as tautomers of each other:

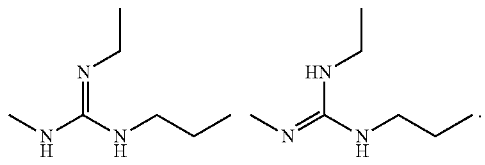

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Discussion of the Present Technology

Prostate-specific membrane antigen ("PSMA")-targeted radiotherapy of prostate cancer (PCa) has emerged recently as a promising approach to the treatment of disseminated disease. While PSMA is expressed by prostate cancer, PSMA is expressed on the neo-vasculature of several other tumor types, including (but not limited to) glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, and renal cell carcinoma. See, e.g., Wernicke A G, Kim S, Liu H, Bander N H, Pirog E C. Prostate-specific Membrane Antigen (PSMA) Expression in the Neovasculature of Gynecologic Malignancies: Implications for PSMA-targeted Therapy. Appl Immunohistochem Mol Morphol. 2016 Feb. 9 (doi. 10.1097/PAI.0000000000000297); Wang H L, Wang S S, Song W H, Pan Y, Yu H P, Si T G, Liu Y, Cui X N, Guo Z. Expression of prostate-specific membrane antigen in lung cancer cells and tumor neovasculature endothelial cells and its clinical significance, PLoS One, 2015 May 15; 10(5):e0125924 (doi: 10.1371/joumal.pone.0125924); Samplaski M K, Heston W, Elson P, Magi-Galluzzi C, Hansel D E. Folate hydrolase (prostate-specific membrane antigen) 1 expression in bladder cancer subtypes and associated tumor neovasculature. Mod Pathol. 2011 November; 24(11):1521-9 (doi: 10.1038/modpathol.2011.112); Haffner M C, Kronberger I E, Ross J S, Sheehan C E, Zitt M, Mühlmann G, Ofner D, Zelger B, Ensinger C, Yang X J, Geley S, Margreiter R, Bander N H. Prostate-specific membrane antigen expression in the neovasculature of gastric and colorectal cancers. Hum Pathol, 2009 December; 40(12):1754-61 (doi: 10.1016/j.humpath.2009.06.003); Baccala A, Sercia L, Li J, Heston W, Zhou M. Expression of prostate-specific membrane antigen in tumor-associated neovasculature of renal neoplasms. Urology. 2007 August; 70(2):385-90 (doi: 10.1016/j.urology.2007.03.025); and Chang S S, Reuter V E, Fleston W D, Bander N H, Grauer L S, Gaudin P B. Five different anti-prostate-specific membrane antigen (PSMA) antibodies confirm PSMA expression in tumor-associated neovasculature. Cancer Res. 1999 Jul. 1; 59(13):3192-8, each of which is incorporated herein by reference.

A small number of ligands have been evaluated in patients, and while early tumor response is encouraging, these compounds localize to the parotid, salivary and lacrimal glands as well as the kidney, leading to dose-limiting toxicities and adverse events affecting quality of life.

In the absence of stable isotopes of astatine, iodine has been utilized as a surrogate for drug development and for predicting radiation dosimetry. Recent work has confirmed that the pharmacokinetics of the small molecule PSMA inhibitor $^{131}$I-DCIBzL and its astatinated analogue (2S)-2-(3-(1-carboxy-5-(4-$^{211}$At-astatohenzamido)pentyl)ureido)-pentanedioic acid ("$^{211}$At-6") were similar in a preclinical prostate cancer model, such as discussed in Kiess A P, Minn I, Vaidyanathan G, et at, (2S)-2-(3-(1-Carboxy-5-(4-[211At]astatobenzamido)pentyl)ureido)-pentanedioic acid for PSMA-targeted α-particle radiopharmaceutical therapy. *J Nucl Med.* 2016; 57:1569-1575 incorporated herein by reference.

Notable is the potential for dose-limiting toxicity in PSMA-targeted radiotherapies. It has been reported that PSMA is expressed at low levels in the parotid and lacrimal glands, and recent experiments have shown that PMPA can be used to displace $^{68}$Ga-PSMA-HBED-CC from rat salivary glands. See O'Keefe D S, Bacich D J, Heston W D W. Comparative analysis of prostate-specific membrane antigen (PSMA) versus a prostate-specific membrane antigen-like gene. *Prostate,* 2004; 58:200-210 and Wüstemann T, Nikolopoulou A, Amor-Coarasa A, et al. Protecting salivary glands: displacement of off-target bound prostate-specific membrane antigen ligands. *Eur J Nucl Med Mol Imaging.* 2016:43(Suppl 1):S15, each of which is incorporated herein by reference. These findings suggest that uptake of radiopharmaceutical s in these structures is PSMA-mediated.

Indeed, dose-limiting toxicity to the salivary glands was observed for $^{131}$I-MIP-1095 and high kidney uptake was also observed for $^{131}$I-MIP-1095 in mice, although this did not prove to be dose-limiting during initial clinical evaluation in human of a single therapy cycle. See Zechmann C M, Afshar-Oromieh A, Armor T, et al. Radiation dosimetry and first therapy results with a $^{124}$I/$^{131}$I-labeled small molecule (MIP-1095) targeting PSMA for prostate cancer therapy. *Eur J Nucl Med Mol Imaging.* 2014; 41:1280-1292, incorporated herein by reference. Moderate xerostomia has been reported for $^{177}$Lu-PSMA-617, but translation of this ligand to targeted α-particle therapy as $^{225}$Ac-PSMA-617 led to severe and sustained xerostomia. See Kratochwil C, Giesel F L, Stefanova M, et al. PSMA-Targeted Radionuclide Therapy of Metastatic Castration-Resistant Prostate Cancer with $^{177}$Lu-Labeled PSMA-617. *J Nucl Med* 2016; 57:1170-1176, Fendler W P, Reinhardt S, Ilhan H, et al. Preliminary experience with dosimetry, response and patient reported outcome after $^{177}$Lu-PSMA-6'17 therapy for metastatic castration-resistant prostate cancer, *Oncotarget.* 2017; 8:3581-3590, and. Kratochwil C, Bruchertseifer F, Giesel F L, et al. $^{225}$Ac-PSMA-617 for PSMA targeting alpha-radiation therapy of patients with metastatic castration-resistant prostate cancer. *J Nucl Med.* 2016; 57:1941-1944, each of which is incorporated herein by reference.

The present technology provides compounds displaying high affinity for PSMA and appropriate affinity for human serum albumin (HSA) (alternately described herein as "double targeted constructs," "double targeted compounds," and "dual targeting ligands") in order to provide a higher therapeutic index and be suitable for treatment of cancer expressing PSMA by targeted alpha therapy (TAT). The present technology is particular suited to treat prostate cancer. Compositions are also provided that incorporating such compounds, as are methods related to the treatment of cancer expressing PSM A. Furthermore, the present technology provides a method of enhancing uptake of a therapeutic agent, such as a double targeted construct, to a tumor presenting PSMA is provided, by modifying the human serum albumin binding moiety of such agents.

Thus, in an aspect, a compound according to Formula I is provided (I)

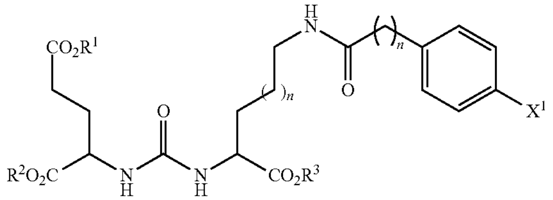

or a pharmaceutically acceptable salt thereof, wherein $X^1$ is $^{124}$I, $^{125}$I, $^{127}$I, $^{131}$I, $^{211}$At, or $Sn(R^4)_3$; $R^1$, $R^2$, and $R^3$ are each independently H, methyl, benzyl, 4-methoxybenzyl, or tert-butyl; $R^4$ is independently at each occurrence an alkyl group; n is 1 or 2; and m is 0, 1, 2, or 3. In any embodiment herein, $R^1$, $R^2$, and $R^3$ may each independently be H or tert-butyl. $R^4$ may independently at each occurrence be methyl, ethyl, propyl, propyl, or butyl. In any embodiment herein, it may be when n is 2, then m is not 2. In any embodiment herein, it may be that $X^1$ is $^{124}$I, $^{123}$I, $^{131}$I, or $^{211}$At. In any embodiment herein, the compound of Formula I may be a compound of Formula Ia (Ia)

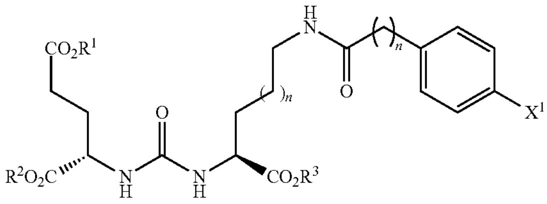

or a pharmaceutically acceptable salt thereof.

In an aspect, a compound of Formula II is provided (II)

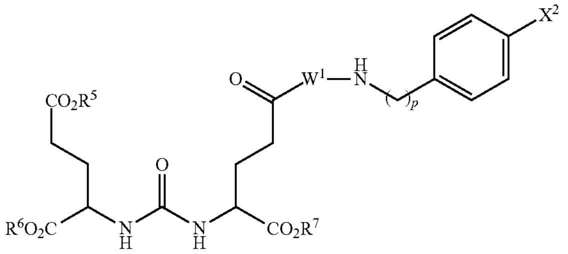

or a pharmaceutically acceptable salt thereof, wherein $X^2$ is $^{124}I$, $^{125}I$, $^{127}I$, $^{131}I$, $^{211}At$, or $Sn(R^8)_3$; $R^5$, $R^6$, and $R^7$ are each independently H, methyl, benzyl, 4-methoxybenzyl, or tert-butyl; $R^8$ is independently at each occurrence an alkyl group; W1 is a bond or —NH-alkylene-; and p is 0, 1, 2, or 3. In any embodiment herein, $R^5$, $R^6$, and $R^7$ may each independently be H or tert-butyl. $W^1$ may be a bond or a carboxylate-substituted alkylene. In any embodiment herein, $W^1$ may be a bond, —NH—CH(C(O)OH)—$(CH_2)_3$—, or —NH—CH(C(O)OH)—$(CH_2)_4$—. In any embodiment herein, it may be that $R^8$ is independently at each occurrence methyl, ethyl, propyl, propyl, or butyl. In any embodiment herein, it may be $X^1$ is $^{124}I$, $^{125}I$, $^{131}I$, or $^{211}At$. In any embodiment herein, the compound of Formula II may be a compound of Formula Ha (IIa)

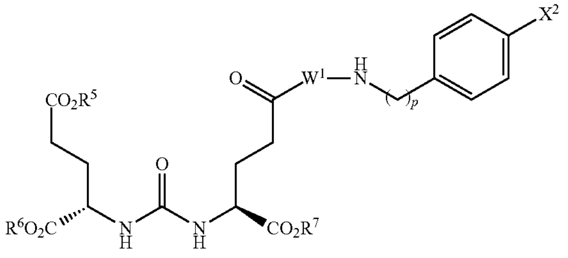

or a pharmaceutically acceptable salt thereof.

In an aspect of the present technology, a composition is provided that includes any one of the aspects and embodiments of compounds of Formulas I-II and a pharmaceutically acceptable carrier. As used herein, a "pharmaceutically acceptable carrier" includes carriers and/or excipients. In a related aspect, a pharmaceutical composition is provided, the pharmaceutical composition including an effective amount of the compound of any one of the aspects and embodiments of compounds of Formulas I-II for treating a condition; and where the condition is cancer expressing PSMA. In a further related aspect, a method is provided that includes administering a compound of any one of the aspects and embodiments of compounds of Formulas I-II (e.g., such as administering an effective amount) or administering a pharmaceutical composition comprising an effective amount of a compound of any one of the aspects and embodiments of compounds of Formulas I-II to a subject suffering from a cancer expressing PSMA. The cancer may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer. The prostate cancer may include castration resistant prostate cancer.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of cancer such as prostate cancer. Another example of an effective amount includes amounts or dosages that are capable of reducing symptoms associated with cancer, such as, for example, reduction of the number of cancer cells in circulation. As used herein, a "subject" or "patient" is a mammal, such as a cat, dog, rodent or primate. Typically the subject is a human, and, preferably, a human suffering from or suspected of suffering from a cancer expressing PSMA, such as prostate cancer. The term "subject" and "patient" can be used interchangeably.

Thus, the instant present technology provides pharmaceutical compositions and medicaments comprising any of the compounds disclosed herein (e.g., compounds of Formulas I-IV) and a pharmaceutically acceptable carrier or one or more excipients or fillers (collectively, such carriers, excipients, fillers, etc., will be referred to as "pharmaceutically acceptable carriers" unless a more specific term is used). The compositions may be used in the methods and treatments described herein. Such compositions and medicaments include a therapeutically effective amount of any compound as described herein, including but not limited to a compound of Formulas I-II, for treating one or more of the herein-described conditions. The pharmaceutical composition may be packaged in unit dosage form. For example, the unit dosage form is effective in treating cancer expressing PSMA when administered to a subject in need thereof. Such cancer expressing PSMA includes one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with cancer expressing PSMA, such as prostate cancer. The compounds and compositions described herein may be used to prepare formulations and medicaments that prevent or treat a variety of disorders associated with such cancer. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present, technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arable, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum, and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. An isotonic solution will be understood as isotonic with the subject. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, the size of a tumor decreases. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of cancer expressing PSMA, such as, for example, reduction in the volume of a tumor, such as prostate cancer-related tumor. Effectiveness of the compositions and methods of the present technology may also be demonstrated by a decrease in the population of cancer cells in circulation.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of cancer expressing PSMA, such as prostate cancer. Thus, a pharmaceutical composition of the present technology may further include an anti-cancer agent different than the compounds of Formulas I-II. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistic-ally be effective for the treatment of cancer expressing PSMA, such as prostate cancer.

In an aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment, of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty-acid or fatty acid ester group, each of which can independently comprise from about eight to about seventy carbon atoms. Conjugates may include polyethylene amine (PEI), polyglycine, hybrids of PEI and polyglycine, polyethylene glycol (PEG) or methoxypolyethylene glycol (mPEG). Conjugates for use with a compound of the present technology can, in one aspect, improve in vivo half-life. Other exemplary conjugates for use with a compound of the present technology as well as applications thereof and related techniques include those generally-described by U.S. Pat. No. 5,672,662, which is hereby incorporated by reference herein.

The present technology provides methods of identifying a target of interest including contacting the target of interest with a detectable or imaging effective quantity of a compound of the present technology. A detectable or imaging effective quantity is a quantity of a compound of the present technology necessary to be detected by the detection method chosen. For example, a detectable quantity can be an administered amount sufficient to enable detection of binding of the labeled compound to a target of interest including, but not limited to, cancer expressing PSMA such as glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and/or prostate cancer. Upon binding of the labeled compound to the target of interest, the target may be isolated, purified and further characterized such as by determining the amino acid sequence of a protein to which the compound of the present technology is bound.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

In an aspect, a method of enhancing uptake of a therapeutic agent to a tumor presenting prostate specific membrane antigen ("PSMA") is provided, where the method includes administering a first therapeutic agent includes a PMSA-targeting moiety and a human serum albumin binding moiety to a subject with one or more cancer tumors expressing PSMA, where the human serum albumin binding moiety includes a radionuclide; detecting distribution of the first therapeutic agent in the subject; and modifying the first therapeutic agent to provide a second therapeutic agent. The second therapeutic agent is, of course, of a different structure than the first therapeutic agent. The second therapeutic agent may therefore be described as including the same PMSA-targeting moiety of the first therapeutic agent and a second human serum albumin binding moiety. The PMSA-targeting moiety may include a glutamate-urea-glutamate moiety or a glutamate-urea-lysine moiety. The cancer expressing PSMA may be one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer. The prostate cancer may be castration resistant prostate cancer.

The human serum albumin binding moiety may include a $^{124}$I-substituted, a $^{125}$I-substituted, a $^{131}$I-substituted, or a $^{211}$At-substituted phenyl moiety. The human serum albumin binding moiety may include a 4-($^{124}$I)-substituted, a 4-($^{125}$I)-substituted, a 4-($^{131}$I)-substituted, or 4-($^{211}$At)-substituted phenyl moiety. The human serum albumin binding moiety may include a 1,4-phenylene where the group at the 4 position is $^{124}$I, $^{125}$I, $^{131}$I, or $^{211}$At. In any embodiment herein, modifying the first therapeutic agent may include lengthening or shortening a hydrocarbon chain of the human serum albumin binding moiety. Modifying the first therapeutic agent may include conjugating a polyalkane glycol (e.g., polyethylene glycol (PEG), polypropylene glycol (PPG), methoxypolyethylene glycol (mPEG)), polyethylene amine (PEI), polyglycine, hybrids of PEI and poly glycine, carbohydrate polymer, amino acid polymer, polyvinyl pyrolidone, a fatty acid, and/or a fatty acid ester group to the human serum albumin binding moiety. The conjugating step may include inserting a polyalkane glycol, polyethylene amine (PEI), polyglycine, carbohydrate polymer, amino acid polymer, polyvinyl pyrolidone, a fatty acid, a fatty acid ester group, or a combination of any two or more thereof between the PSMA-targeting moiety and the human serum albumin binding moiety. The conjugating step may include conjugating a polyalkane glycol, polyethylene amine (PEI), polyglycine, carbohydrate polymer, amino acid polymer, polyvinyl pyrolidone, a fatty acid, a fatty acid ester group, or a combination of any two or more thereof at a position on the human serum albumin binding moiety that is distal to the PSMA-targeting moiety. In any embodiment herein, the first therapeutic agent may be a compound of Formula I or II; in any embodiment herein, the second therapeutic agent may be a compound of Formula I or II.

The method may include administering the second therapeutic agent to a subject with one or more cancer tumors expressing PSMA and detecting distribution of the second therapeutic agent in the subject. Due to the modification of the first therapeutic agent, the second therapeutic agent, may exhibit a higher tumor uptake in comparison with non-tumor tissues of the subject than was exhibited by the first therapeutic agent. In any embodiment of the method, it may be that administering the first therapeutic agent includes parenteral administration, such as intravenous administration and/or intra-arterial administration.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

Examples

General Synthetic and Analytical Details:

All solvents were purchased from Sigma Aldrich and were of reagent grade quality unless otherwise indicated. Solvents were dried either by distillation over an activated stainless steel column (Pure Process Technology, LLC) column or by drying over activated molecular sieves. Reagents were purchased from Sigma Aldrich or Alfa Aesar and were of reagent grade. All reactions described below were carried out in dried glassware. Purifications were performed using silica chromatography on VWR® High Purity Silica Gel 60 Å or flash chromatography using a CombiFlash Rf+(Teledyne Isco). Preparative HFLC was performed using an XBridge™ Prep C18 5 μm OBD™ 19×100 mm column (Waters) on a dual pump Agilent ProStar HPLC fitted with an Agilent ProStar 325 Dual Wavelength UV-Vis Detector. UV absorption was monitored at 220 nm and 280 nm. A binary solvent system was used, with solvent A comprising $H_2O$+0.01% TFA and solvent B consisting of 90% v/v MeCN/$H_2O$+0.01% TFA. Purification was achieved at a flow rate of 12 mL/min and with the following gradient HPLC method: 0% B 0-1 min., 0-100% B 1-28 mins, 100-0% B 28-30 mins. Final products were identified and characterized using thin layer chromatography, analytical HPLC, mass spectroscopy and NMR spectroscopy. Analytical HPLC was performed using an XSelect™ CSH™ C18 5 μm 4.6×50 mm column (Waters) at a flow rate of 2 mL/min and a gradient of 0-100% B over 10 min. Mass determinations were performed by LCMS analysis using a Waters ACQUITY UPLC® coupled to a Waters SQ Detector 2. NMR analyses were performed using a Bruker Avance III 500 MHz spectrometer. Spectra are reported as ppm and are referenced to the solvent resonances in DMSO-d6 or chloroform-d (Sigma Aldrich). The purity of all compounds evaluated in the biological assay was >95% purity as judged by LC-MS and $^{1}$H NMR.

Representative Synthesis of Compounds of the Present Technology. Representative synthetic procedures are provided below in Scheme 1. In these exemplary compounds, the use of iodine and/or radioiodine is to be further understood as a surrogate for the radiohalogen $^{211}$At. See Kelly, J. M., Amor-Coarasa, A., Nikolopoulou, A., Wüstemann, T., Barelli, P., Kim, D., Williams, C, Jr, Zheng, X., Br C., Hu, B., Warren, J. D., Hage, D. S., DiMagno, S. G., and Babich, J. W. Double Targeting Ligands with Modulated Pharmacokinetics for Endoradiotherapy of Prostate Cancer, *J. Nucl. Med.* (Apr. 27, 2017) (doi: 10.2967/jnumed.116.188722), incorporated herein by reference.

Scheme 1.
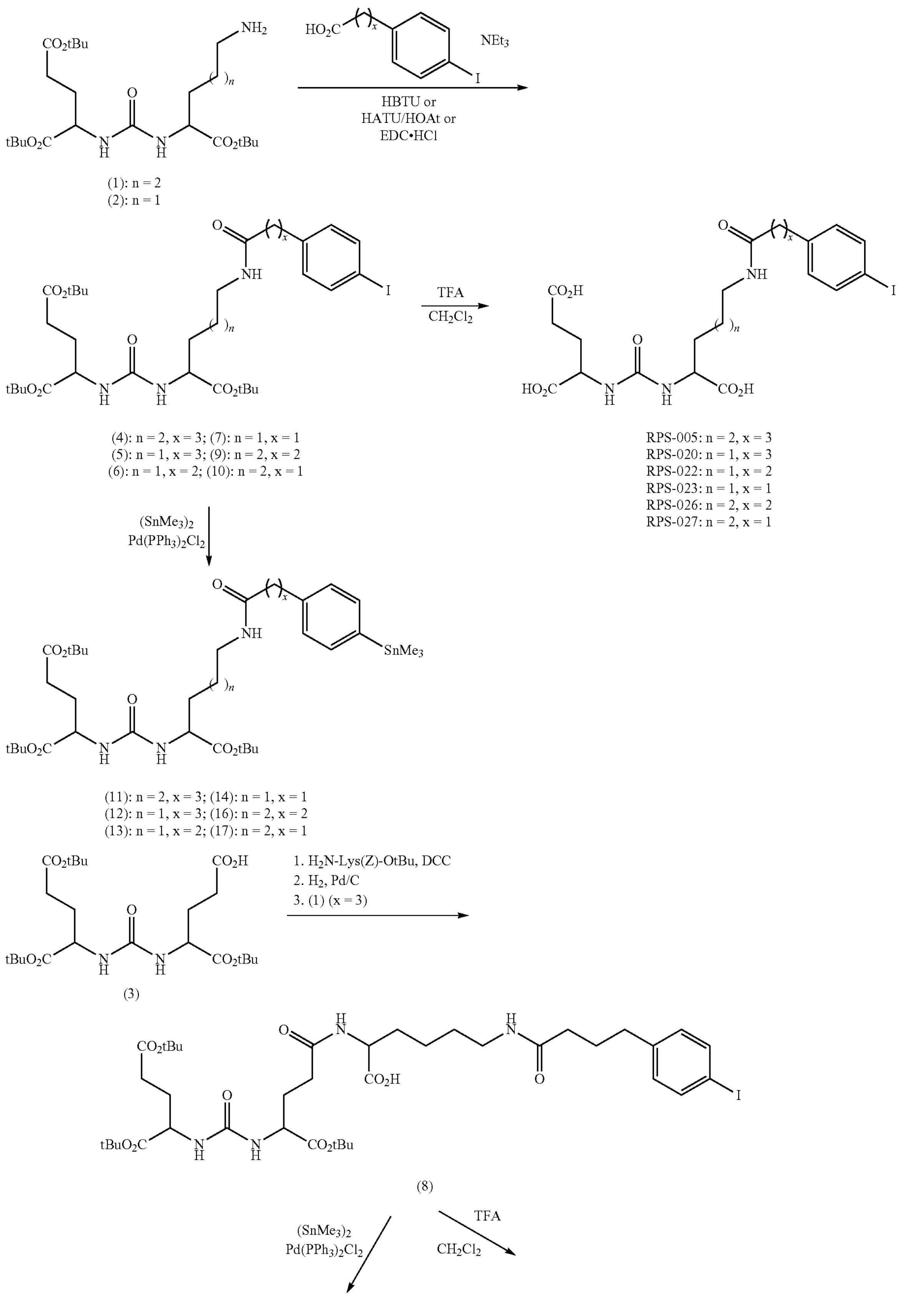
(1): n = 2
(2): n = 1
(4): n = 2, x = 3; (7): n = 1, x = 1
(5): n = 1, x = 3; (9): n = 2, x = 2
(6): n = 1, x = 2; (10): n = 2, x = 1
RPS-005: n = 2, x = 3
RPS-020: n = 1, x = 3
RPS-022: n = 1, x = 2
RPS-023: n = 1, x = 1
RPS-026: n = 2, x = 2
RPS-027: n = 2, x = 1
(11): n = 2, x = 3; (14): n = 1, x = 1
(12): n = 1, x = 3; (16): n = 2, x = 2
(13): n = 1, x = 2; (17): n = 2, x = 1
(3)
(8)

-continued

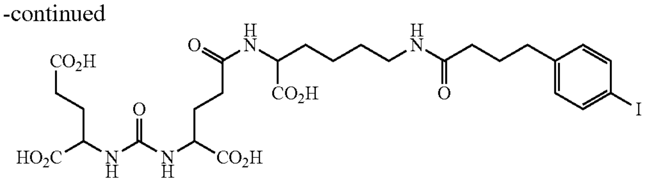

RPS-025

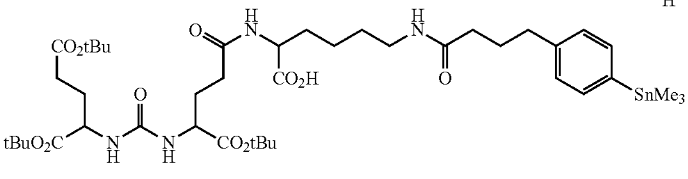

(15)

The synthesis of exemplary compounds are provided below.

Di-tert-butyl (((S)-6-amino-1-(tert-butoxy)-1-oxohexan-2-yl)carbamoyl)-L-glutamate (EuK·3OtBu) (1)

The title compound was synthesized according to protocols described in Maresca K P, Hillier S M, Femia F J, Barone D K C, Joyal J L, Zimmerman C N, Kozikowski A P, Barrett J A, Eckelman W C, Babich J W. A series of halogenated heterodimeric inhibitors of prostate specific membrane antigen (PSMA) as radiolabeled probes for targeting prostate cancer. *J. Med. Chem.* 2009; 52:347-357, incorporated herein by reference. H-Glu(OtBu)-OtBu·HCl (2.96 g, 10 mmol) was suspended in $CH_2Cl_2$ (20 mL) at 0° C. and stirred under Ar. To the stirred suspension was added DMAP (50 mg, 0.4 mmol) and $NEt_3$ (3.6 mL, 25.7 mmol). The resulting mixture was stirred for 5 min at 0° C. Then a fine suspension of 2-carbonyldiimidazole (1.78 g, 11 mmol) in $CH_2Cl_2$ (15 mL) was added, and the reaction was stirred overnight under Ar with warming to rt. It was then diluted with $CH_2Cl_2$ (30 mL) and washed with saturated $NaHCO_3$ solution. $H_2O$ (×2) and saturated NaCl solution. The organic fraction was dried over $MgSO_4$, filtered and concentrated under reduced pressure to give a clear oil. This crude product was purified by flash chromatography (EtOAc/hexane; 0-10% EtOAc over 12 min, then 10-30% EtOAc from 12-16 min, then 30% EtOAc from 16-20 min), and di-tert-butyl (1H-imidazole-1-carbonyl)-L-glutamate (Eu·2OtBu) was isolated as a clear oil (2.14 g; 61%).

To a solution of compound Eu·2OtBu (293 mg, 0.83 mmol) in 1,2-dichloroethane (6 mL) cooled to 0° C. was added MeOTf (93 μL, 0.85 mmol) and $NEt_3$ (237 μL, 1.70 mmol), and the resulting mixture was stirred for 30 min under Ar. Then H-Lys(Z)-OtBu·HCl (310 mg, 0.83 mmol) was added in one portion and the reaction was stirred for 4 h at 40° C., It was then cooled to rt and concentrated under reduced pressure. The crude product was dissolved in $CH_2Cl_2$ (15 mL), washed with 1% v/v AcOH solution, dried over $MgSO_4$, filtered and concentrated under reduced pressure to give an oil. The oil was purified by silica chromatography (EtOAc:hexane=1:1) to give tri-tert-butyl (9S, 13S)-3,11-dioxo-1-phenyl-2-oxa-4,10,12-triazapentadecane-9,13,15-tricarboxylate (EuK(Z)·3OtBu) as a colorless oil that partially solidified upon standing (284 mg; 55%).

To a solution of EuK(Z)·3OtBu (284 mg, 0.46 mmol) in EtOH (6 mL) was added 10% palladium on carbon (8 mg). The suspension was heated to 40° C. and stirred overnight under an $H_2$ atmosphere. Then the reaction was cooled to rt and filtered through celite. The celite was washed with MeOH and the organic layers were combined and concentrated under reduced pressure to give EuK·3OtBu (1) as a colorless oil (95 mg; 44%).

Di-tert-butyl (((S)-5-amino-1-(tert-butoxy)-1-oxopentan-2-yl)carbamoyl)-L-glutamate (EuO.3OtBu) (2)

A solution of MeOTf (248 μL, 2.27 mmol) and $NEt_3$ (700 μL, 5.00 mmol) in 1,2-dichloroethane (3 mL) was added to a solution of 794 mg (2.25 mmol) Eu·2OtBu in 1,2-dichloroethane (7 mL) at 0° C. under Ar. The mixture was stirred at 0° C. for 30 min before MeOTf (124 μL, 0.1.14 mmol) was added. The resulting mixture was stirred for an additional 30 min at 0° C., then H-Orn(Z)-OtBu·HCl (807 mg, 2.25 mmol) was added in one portion and the reaction was heated to 40° C. for 3 h. It was then cooled to rt and washed with $H_2O$. The organic layer was dried over $MgSO_4$, filtered and concentrated under reduced pressure to give a colorless oil. The oil was purified by flash chromatography (50% EtOAC in hexane to 100% EtOAc over 15 min) to give the product tri-tert-butyl (8<S,12S)-3,10-dioxo-1-phenyl-2-oxa-4,9,11-triazatetradecane-8,12,14-tri carboxylate (EuO (Z).3OtBu) as a clear oil (950 mg; 69%). 'H NMR (500 MHz, $CDCl_3$) δ 7.35-7.30 (m, 5H), 5.13 (m, 3H), 5.09 (s, 2H), 4.34 (m, 2H), 3.21 (m, 2H), 2.30 (m, 2H), 2.09 (m, 1H), 1.86 (m, 2H), 1.66-1.56 (m, 3H), 1.45 (s, 18H), 1.44 (s, 9H). ESI(+)=608.5 $[M+H]^+$. Calculated mass: 607.8.

EuO(Z).3OtBu (950 mg, 1.56 mmol) was dissolved in EtOH (10 mL) and transferred to a round bottom flask containing 10% palladium on carbon (12 mg). The suspension was stirred overnight at rt under $H_2$ atmosphere, and was then filtered through celite. The celite was washed with MeCN, and the combined organic fractions were concentrated under reduced pressure. The product EuO.3OtBu (2) was isolated as a white foam (600 mg; 81%). $^1$H NMR (500 MHz, $CDCl_3$) δ 8.20 (br s, 211), 6.43 (d, 1H, J=7.7 Hz), 6.28 (d, 1H, J=8.1 Hz), 4.35 (m, 2H), 3.10 (m, 2H), 2.34 (m, 2H), 2.07 (m, 2H), 1.85 (m, 4H), 1.45 (s, 18H), 1.43 (s, 9H). ESI(+)=474.6 $[M+H]^+$. Calculated mass: 473.3.

(S)-5-(tert-Butoxy)-4-(3-((S)-1,5-di-tert-butoxy-1,5-dioxopentan-2-yl)ureido)-5-oxopentanoic acid (EuE.3OtBu) (3)

To a solution of Eu·2OtBu (200 mg, 0.57 mmol) in 1,2-dichloroethane (8 mL) cooled to 0° C. were added solutions of MeOTf (66 μL, 0.60 mmol) in 1,2-dichloroethane (1 mL) and $NEt_3$ (158 μL, 1.13 mmol) in 1,2-dichloroethane (1 mL). The resulting mixture was stirred for 30 min under Ar, warming to rt. Then H-Glu(OBzl)-OtBu·HCl (188 mg, 0.57 mmol) was added in one portion and the reaction mixture was stirred at rt for 3 h. The reaction was washed with $H_2O$ and the organic layer was dried over $MgSO_4$, filtered and concentrated under reduced pressure to give a clear oil, EuE(OBz).3OtBu (240 mg; 73%), that was used without further purification. $^1$H NMR (500 MHz, $CDCl_3$) δ 7.38-7.32 (m, 5H), 5.12 (d, 2H, J=3.0 Hz), 5.03 (m, 2H), 4.37 (m, 1H), 4.32 (m, 1H), 2.53-2.21 (m, 4H), 2.11 (m, 1H), 2.04 (m, 1H), 1.92 (m, lit), 1.85 (m, 1H), 1.46 (s, 9H), 1.45 (s, 9H), 1.44 (s, 9H). ESI(+)=579.6 $[M+H]^+$. Calculated mass: 578.3.

To a solution of EuE(OBz).3OtBu (210 mg, 0.36 mmol) in EtOH (5 mL) was added 10% palladium on carbon (14 mg) while $N_2$ was bubbled through the solution. The suspension was stirred for 4 h under $H_2$ atmosphere and then filtered through celite and concentrated under reduced pressure to give EuE.3OtBu (3) as a colorless oil (178 mg; 99%). $^1$H NMR (500 MHz, $CDCl_3$) δ 4.37 (m, 1H), 4.29 (m, 1H), 2.40 (m, 2H), 2.29 (m, 2H), 2.14 (m, 1H), 2.07 (m, 1H), 1.85 (m, 2H), 1.46 (s, 9H), 1.44 (s, 9H), 1.42 (s, 9H). ESI(+)=489.4 $[M+H]^+$, Calculated mass: 488.3.

(((S)-1-Carboxy-5-(4-(4-iodophenyl)butanamido) pentyl)carbamoyl)-L-glutamic acid (RPS-005)

To a solution of 90 mg (185 μmol) EuK·3OtBu (1) in $CH_2Cl_2$ (5 mL) was added a solution of 4-(4-iodophenyl) butanoic acid (54 mg, 185 μmol) and EDC (34 mg, 221 μmol) in $CH_2Cl_2$. (5 mL). The mixture was stirred for 10 min, then DIPEA (38 μL, 221 μmol) was added and the reaction was stirred at it for 4 h. The mixture was diluted with $CH_2Cl_2$ (10 mL) and washed with 1N HCl (10 mL), saturated $NaHCO_3$ (10 mL), and brine (20 mL). The organic layer was dried over $Na_2SO_4$ and concentrated to afford the crude product. The crude product was purified by flash chromatography (0-100% EtOAc in hexane), and EuK-IPBA·3OtBu (4) was isolated as a white solid (96 mg, 68%). $^1$H NMR (500 MHz, $CDCl_3$) δ 7.54 (d, 2H, J=8.1 Hz), 6.91 (d, 2H, J=8.1 Hz), 6.67 (m, 1H), 5.81 (d, 1H, J=8.1 Hz), 5.58 (d, 1H, J=7.7 Hz), 4.30 (m, 1H), 4.18 (m, 1H), 3.23 (m, 1H), 3.13 (m, 1H), 2.56 (t, 2H, J=7.6 Hz), 2.29 (m, 2H), 2.18 (t, 2H, J=7.4 Hz), 2.05 (m, 1H), 1.90 (m, 2H), 1.80 (m, 1H), 1.70 (m, 1H), 1.51-1.44 (m, 3H), 1.41 (s, 9H), 1.38 (s, 18H), 1.28 (m, 2H). ESI(+)=760.2 $[M+H]^+$. Calculated mass: 759.3.

EuK-IPBA·3OtBu (4) (75 mg, 99 μmol) was dissolved in 2 mL $CH_2Cl_2$ and 2 mL TFA and stirred for 3 h at it. The solvent was removed under a stream of $N_2$ and the crude product was purified by prep HPLC (15% B to 100% B). The peak corresponding to the product was collected and lyophilized and RPS-005 was isolated as a white solid residue (33 mg; 57%). $^1$H NMR (500 MHz, DMSO) δ 7.76 (m, 1H), 7.62 (d, 2H, J=7.7 Hz), 7.01 (d, 2H, J=7.6 Hz), 6.30 (m, 2H), 4.09 (m, 1H), 4.04 (m, 1H), 3.00 (m, 2H), 2.50 (2H), 2.26 (m, 2H), 2.04 (t, 2H, J=7.3 Hz), 1.91 (m, 1H), 1.75 (m, 3H), 1.64 (m, 1H), 1.53 (m, 1H), 1.38 (m, 2H), 1.27 (m, 2H), ESI(+) 592.2=$[M+H]^+$. Calculated mass: 591.1.

(((S)-1-Carboxy-4-(4-(4-iodophenyl)butanamido) pentyl)carbamoyl)-L-glutamic add (RPS-020)

To a stirred suspension of 4-(p-iodophenyl)butyric acid (93 mg, 0.32 mmol) and HBTU (151 mg, 0.40 mmol) in $CH_2Cl_2$ (3 mL) was added a solution of $NEt_3$ (56 μL, 0.40 mmol) in $CH_2Cl_2$ (4 mL), and the resulting mixture was stirred at rt under Ar for 5 min. Then a solution of EuO.3OtBu (2) (150 mg, 0.32 mmol) in $CH_2Cl_2$ (3 mL) was added, and the reaction was stirred overnight at rt. The solvent was evaporated under reduced pressure, and the crude product was purified by flash chromatography (100% hexane to 100% EtOAc over 12 min). The product EuO-IPBA·3OtBu (5) was isolated as a pale oil (125 mg; 52%). $^1$H NMR (500 MHz, $CDCl_3$) δ 7.59 (d, 2H, J=8.3 Hz), 6.95 (d, 2H, J=8.3 Hz), 6.28 (br s, 1H), 5.35 (d, 1H, J=8.2 Hz), 5.30 (d, 1H, J=7.9 Hz), 4.32 (m, 2H), 3.26 (m, 2H), 2.60 (t, 2H, J=7.7 Hz), 2.33 (m, 2H), 2.19 (t, 2H, J=7.5 Hz), 2.07 (m, 1H), 1.95 (quint, 2H, J=7.3 Hz), 1.83 (m, 1H), 1.75 (m, 1H), 1.60 (m, 1H), 1.56 (m, 2H), 1.47 (s, 9H), 1.45 (s, 9H), 1.44 (s, 9H). ESI(+)=746.5 $[M+H]^+$. Calculated mass: 745.3.

EuO-IPBA·3OtBu (5) (30 mg, 40 μmol) was dissolved in 1 mL $CH_2Cl_2$ and 1 mL TFA and stirred overnight at rt. The solvent was removed under a stream of $N_2$ and the crude product was purified by prep HPLC (15% B to 100% B). The peak corresponding to the product was collected and lyophilized and RPS-020 was isolated as a white solid residue (19 mg; 82%), $^1$H NMR (500 MHz, DMSO) δ 7.83 (t, 1H, J=5.6 Hz), 7.65 (d, 2H, J=8.3 Hz), 7.03 (d, 2H, J=8.3 Hz), 6.36 (d, 1H, J=8.2 Hz), 6.31 (d, 1H, J=8.2 Hz), 4.12 (m, 1H), 4.07 (m, 1H), 3.04 (m, 2H), 2.51 (t, 2H, J=7.7 Hz), 2.25 (m, 2H), 2.06 (t, 2H, J=7.5 Hz), 1.95 (m, 1H), 1.81-1.66 (m, 4H), 1.53 (m, 1H), 1.41 (m, 1H) ESI(+)=578.2 $[M+H]^+$; ESI(−) =576.3 $[M-H]^-$ Calculated mass: 577.1.

(((S)-1-Carboxy-4-(3-(4-iodophenyl)propanamido) pentyl)carbamoyl)-L-glutamic acid (RPS-022)

To a solution of 3-(p-iodophenyl)propanoic acid (63 mg, 0.22 mmol) and EDC.HCl (57 mg, 0.30 mmol) in $CH_2Cl_2$ (5 mL) was added $NEt_3$ (84 μL, 0.60 mmol) and the reaction was stirred at rt under Ar for 30 min. Then a solution of EuO.3OtBu (2) (103 mg, 0.22 mmol) in $CH_2Cl_2$ (1 mL) was added and the reaction was stirred overnight at rt under Ar. The reaction was diluted with 10 mL $CH_2Cl_2$ and washed successively with $H_2O$ and saturated NaCl solution. The organic layer was dried over $MgSO_4$, filtered and concentrated under reduced pressure to give the crude product as a pale oil. The crude product was purified by flash chromatography (100% hexane to 100% EtOAc over 20 min), and EuO-IPPA·3OtBu (6) was isolated as a clear oil (87 mg; 53%). $^1$H NMR (500 MHz, $CDCl_3$) δ 7.57 (d, 2H, J=8.2 Hz), 6.96 (d, 2H, J=8.2 Hz), 6.61 (br s, 1H), 5.61 (d, 1H, J=8.2 Hz), 5.44 (d, 1H, J=7.8 Hz), 4.34 (m, 1H), 4.23 (m, 1H), 3.29-3.16 (m, 2H), 2.90 (t, 2H, J=7.8 Hz), 2.46 (t, 2H, J=7.8 Hz), 2.27 (m, 2H), 2.09 (m, 1H), 1.85 (m, 1H), 1.73 (m, 1H), 1.58-1.40 (m, 3H), 1.46 (s, 9H), 1.42 (s, 18H). ESI(+)=732.4 $[M+H]^+$. Calculated mass: 731.3.

EuO-IPPA·3OtBu (6) (7.7 mg, 10.5 μmol) was dissolved $CH_2Cl_2$ (1 mL) and TEA (1 mL) and stirred overnight at rt. The solvent was removed under a stream of $N_2$ and the crude residue was lyophilized to give RPS-022 as a white solid residue (2.5 mg; 42%). $^1$H NMR (500 MHz, DMSO) δ 7.84 (t, 1H, J=5.6 Hz), 7.60 (d, 2H, J=8.3 Hz), 7.01 (d, 2H, J=8.3 Hz), 6.34 (d, 1H, J=8.3 Hz), 6.29 (d, 1H, J=8.3 Hz), 4.09 (m, 1H), 4.04 (m, 1H), 3.00 (m, 2H), 2.75 (t, 2H, J=7.8 Hz), 2.32 (t, 2H, J=7.8 Hz), 2.23 (m, 2H), 1.91 (m, 1H), 1.71 (m, 1H), 1.62 (m, 1H), 1.49 (m, 1H), 1.38 (m, 2H). ESI(+)=564.1 $[M+H]^+$; 562.2 $[M-H]^-$. Calculated mass: 563.1.

(((S)-1-Carboxy-4-(2-(4-iodophenyl)acetamido)pentyl)carbamoyl)-L-glutamic add (RPS-023)

To a stirred suspension of 2-(p-iodophenyl)acetic acid (26 mg, 0.10 mmol) and HBTU (50 mg, 0.13 mmol) in $CH_2Cl_2$.

(3 mL) was added a solution of EuO.3OtBu (2) (50 mg, 0.11 mmol) and $NEt_3$ (19 μL, 0.13 mmol) in $CH_2Cl_2$ (0.5 mL), and the resulting mixture was stirred overnight at rt under Ar. The solvent was removed under reduced pressure and the crude residue was purified by silica chromatography (33% EtOAc in hexane to 0.100% EtOAc). EuO-IPAA·3OtBu (7) was isolated as a clear oil (48 mg; 67%). $^1H$ NMR (500 MHz, MeOD) δ 7.58 (d, 2H, J=8.4 Hz), 7.02 (d, 2H, J=8.4 Hz), 4.14 (m, 1H), 4.09 (m, 1H), 3.39 (s, 2H), 3.14 (t, 2H, J=6.7 Hz), 2.26 (m, 2H), 1.99 (m, 1H), 1.77 (m, 1H), 1.69 (m, 1H), 1.50 (m, 3H), 1.42 (s, 9H), 1.41 (s, 18H). ESI(+)=718.4 $[M+H]^+$. Calculated mass: 717.3.

EuO-IPAA·3OtBu (7) (10 mg, 14 μmol) was dissolved in $CH_2Cl_2$ (1 mL) and TFA (1 mL) and stirred at rt for 4 h. The solvent was removed under a stream of $N_2$ and the crude product was lyophilized to give RPS-023 as a white solid residue (6.2 mg; 81%). $^1H$ NMR (500 MHz, DMSO) δ 8.08 (t, 1H, J=5.4 Hz), 7.64 (d, 2H, J=8.2 Hz), 7.05 (d, 2H, J=8.2 Hz), 6.32 (m, 2H), 4.08 (m, 2H), 3.34 (s, 2H), 3.03 (m, 2H), 2.23 (m, 2H), 1.91 (m, 1H), 1.72-1.62 (m, 2H), 1.51 (m, 1H), 1.41 (m, 2H). ESI(+)=550.2 $[M+H]^+$; 548.2 $[M-H]^-$ Calculated mass: 549.1.

(3S,7S,12S)-21-(4-iodophenyl)-5,10,18-trioxo-4,6,11,17-tetraazahenicosane-1,3,7,12-tetracarboxylic acid (RPS-025)

A solution of EuE.3OtBu (3) (140 mg, 0.29 mmol) and EDC.HCl (60 mg, 0.32 mmol) in 1,2-dichloroethane (5 mL) was stirred at if under Ar for 30 min. Then a fine suspension of $H_2N$-Lys(CBz)-OtBu·HCl (108 mg, 0.29 mmol) and $NEt_3$ (126 uL, 0.70 mmol) in 1,2-dichloroethane (5 mL) was added and the mixture was stirred overnight at rt under Ar. The reaction was diluted with $CH_2Cl_2$ (5 mL) and poured into $H_2O$ (10 mL). The layers were separated and the organic layer was washed with saturated NaCl solution, dried over $MgSO_4$, filtered and concentrated under reduced pressure to give a pale oil. The crude product was purified by flash chromatography (0% to 100% EtOAc in hexanes over 11 min, then 100% EtOAc for 7 min) and tetra-tert-butyl (9S,14S,18S)-3,11,16-trioxo-1-phenyl-2-oxa-4,10,15,17-tetraazaicosane-9,14,18,20-tetracarboxylate (EuEK(Z).4OtBu) was isolated as a clear oil (94 mg; 41%). $^1H$ NMR (500 MHz, $CDCl_3$) δ 7.36-7.23 (m, 6H), 5.93 (d, 1H, J=8.4 Hz), 5.30 (d, 1H, J=8.8 Hz), 5.08 (d, 1H, J=8.7 Hz), 5.06 (s, 2H), 4.43 (m, 1H), 4.35 (m, 1H), 4.24 (m, 1H), 3.16 (m, 2H), 2.29-2.22 (m, 3H), 2.17-2.07 (m, 2H), 2.04 (m, 1H), 1.90 (m, 1H), 1.73 (m, 2H), 1.63 (m, 1H), 1.46-1.39 (m, 4H), 1.45 (s, 9H), 1.44 (s, 9H), 1.42 (s, 9H), 1.41 (s, 9H) ESI(+)=807.8 $[M+H]^+$. Calculated mass: 806.5.

EuEK(Z).4OtBu (37 mg, 46 μmol) was dissolved in EtOH (4 mL). Then 10% palladium on carbon (8 mg) was added and the suspension was stirred overnight under $H_2$ atmosphere. The mixture was filtered through celite and the filtrate was concentrated under reduced pressure to give EuEK.4OtBu as a clear oil that solidified upon standing (24 mg; 78%). $^1H$ NMR (500 MHz, $CDCl_3$) δ 8.19 (br s, 2H), 7.65 (br s, 1H), 6.27 (m, 2H), 4.32 (m, 2H), 4.10 (m, 1H), 3.06 (m, 2H), 2.39 (m, 2H), 2.33 (m, 2H), 2.02 (m, 111), 1.96 (m, 1H), 1.78 (m, 4H), 1.56-1.39 (m, 4H), 1.44 (s, 18H), 1.42 (s, 1811) ESI(+)=673.7 $[M+H]^+$. Calculated mass: 672.4.

4-(p-Iodophenyl)butyric acid (580 mg, 2.0 mmol) and N-hydroxysuccinimide (345 mg, 3.0 mmol) were dissolved in $CH_2Cl_2$ (10 mL) and cooled to 0° C. under Ar. A solution of DCC (620 mg, 3.0 mmol) in $CH_2Cl_2$. (4 mL) was added dropwise over 10 min, and the reaction was warmed to rt and stirred overnight at rt. The reaction was filtered to remove the insoluble urea by-product, and the filter cake was washed with $CH_2Cl_2$. The organic fractions were combined and concentrated under reduced pressure, and the crude product was purified by silica chromatography (EtOAC:hexane=1:1) to give A-succinimidyl 4-(p-iodophenyl)butanoate as a white solid (400 mg, 52%). $^1H$ NMR (500 MHz, $CDCl_3$) δ 7.61 (d, 2H, J=8.2 Hz), 6.96 (d, 2H, J=8.2 Hz), 2.85 (br s, 4H), 2.68 (t, 2H, J=7.6 Hz), 2.60 (t, 2H, J=7.3 Hz), 2.04 (quint, 2H, J=7.4 Hz).

A solution of DIPEA (45 μL, 0.25 mmol) in 1,2-dichloroethane (1 mL) was added to a solution of EuEK.4OtBu (80 mg, 0.12 mmol) and A-succinimidyl 4-(p-iodophenyl)butanoate (46 mg, 0.12 mmol) and stirred overnight at rt under Ar. The mixture was concentrated under reduced pressure and the crude residue was purified by silica chromatography (20%-100% EtOAc in hexane). The product EuEK-IPBA·4OtBu (8) was isolated as a clear oil that solidified upon standing (58 mg; 52%). $^JH$ NMR (500 MHz, $CDCl_3$) δ 7.57 (d, 2H, J=8.2 Hz), 7.22 (d, 1H, J=7.6 Hz), 6.92 (d, 2H, J=8.2 Hz), 5.91 (m, 2H), 5.32 (d, 1H, J=8.8 Hz), 4.42 (m, 1H), 4.30 (m, 1H), 4.25 (m, 1H), 3.20 (m, 2H), 2.57 (t, 2H, J=7.6 Hz), 2.32 (t, 2H, J=7.6 Hz), 2.26 (m, 1H), 2.20-2.10 (m, 5H), 2.03 (m, 1H), 1.94-1.90 (m, 3H), 1.77 (m, 2H), 1.64 (m, 1H), 1.50-1.38 (m, 4H), 1.45 (s, 18H), 1.43 (s, 9H), 1.42 (s, 9H). ESI(+)=945.1 $[M+H]^+$. Calculated mass: 944.4.

EuEK-IPBA·4OtBu (8) (1.9 mg, 2.0 μmol) was dissolved in $CH_2Cl_2$ (0.5 mL) and TEA (0.5 mL) and stirred overnight at rt. The solvent was removed under a stream of $N_2$ and the crude product was diluted in $H_2O$ and purified by prep HPLC. The fraction containing the desired product was collected and lyophilized to give RPS-025 as a white powder (1.4 mg; 97%). $^1H$ NMR (500 MHz, DMSO) δ 7.81 (br s, 1H), 7.64 (d, 2H, J=8.2 Hz), 7.02 (d, 2H, J=8.2 Hz), 6.56 (s, 1H), 6.37 (m, 2H), 4.12 (m, 3H), 3.02 (m, 2H), 2.51 (t, 2H, J=7.6 Hz), 2.28-2.17 (m, 4H), 2.05 (t, 2H, J=7.5 Hz), 1.93 (m, 2H), 1.78-1.63 (m, 5H), 1.57 (m, 1H), 1.37 (m, 2H), 1.29 (m, 2H). ESI(+)=721.1 $[M+H]^+$. Calculated mass: 720.2.

(((S)-1-Carboxy-5-(3-(4-iodophenyl)propanamido)pentyl)carbamoyl)-L-glutamic add (RPS-026)

To a solution of 3-(p-iodophenyl)propanoic acid (85 mg, 0,308 mmol), HO At (0.6M in THF, 0.51 mL, 0.308 mmol) and HATU (175 mg, 0.461 mmol) in DMF (1 mL) cooled to 0° C. under Ar was added a solution of EuK·3OtBu (1) (150 mg, 0.308 mmol) in DMF (1 mL). The mixture was stirred for 10 min, then (0.107 mL, 0.615 mmol) DIPEA. The reaction was stirred for 20 min at 0° C., and then for a further 3 h while warming to it. The mixture was diluted with EtOAC (25 mL) and washed with 1N HCl, saturated $NaHCO_3$ solution and saturated NaCl solution. The organic layer was dried over $Na_2SO_4$, filtered and concentrated under reduced pressure. The crude product was purified by flash chromatography (0%-100% EtOAc in hexanes) and EuK-IPPA·3OtBu (9) was isolated as a clear oil (163 mg, 71%). $^1H$ NMR (500 MHz, DMSO) δ 7.83 (m, 1H), 7.61 (d, 2H, J=8.0 Hz), 7.00 (d, 2H, J=7.9 Hz), 6.29 (d, 2H, J=6.5 Hz)), 6.20 (d, 2H, J=6.4 Hz), 4.04 (m, 1H), 3.93 (m, 1H), 2.98 (m, 2H), 2.73 (t, 2H, J=8.2 Hz), 2.31 (t, 2H, J=8.0 Hz), 2.19 (m, 2H), 1.85 (m, 1H), 1.64 (m, 1H), 1.58 (m, 1H), 1.48 (m, 1H), 1.37 (s, 27H), 1.32 (m, 2H), 1.21 (m, 2H). ESI(+)=746.1 $[M+H]^+$. Calculated mass: 745.3.

EuK-IPPA·3OtBu (9) (50 mg, 67 μmol) was dissolved in $CH_2Cl_2$ (3 mL) and TEA (3 mL) and stirred at rt under Ar for 3 h. The solvent was removed under a stream of $N_2$ and the crude product was purified by prep HPLC. The peak corresponding to the product was collected and lyophilized, and RPS-026 was isolated as a white solid residue (15.5 mg, 40%), $^1$H NMR (500 MHz, DMSO) δ 7.80 (m, 1H), 7.61 (d, 2H, J=7.9 Hz), 7.01 (d, 2H, J=8.0 Hz), 6.31 (m, 2H), 4.12 (m, 1H), 4.05 (m, 1H), 2.96 (m, 2H), 2.74 (t, 2H, J=8.1 Hz), 2.32 (t, 2H, J=8.0 Hz), 2.21 (m, 2H), 1.86 (m, 1H), 1.70 (m, 1H), 1.64 (m, 1H), 1.47 (m, 1H), 1.32 (m, 2H), 1.21 (m, 2H). ESI(+)=578.0 [M+H]$^+$. Calculated mass: 577.1.

(((S)-1-Carboxy-5-(2-(4-iodophenyl)acetamido)pentyl)carbamoyl)-L-glutamic add (RPS-027)

To a solution of 2-(p-iodophenyl)acetic acid (81 mg, 0.308 mmol), HOAt (0.6M in THF, 0.51 mL, 0.308 mmol) and HATU (175 mg, 0.461 mmol) in DMF (1 mL) cooled to 0° C. under Ar was added a solution of EuK·3OtBu (1) (150 mg, 0.308 mmol) in DMF (1 mL), The mixture was stirred for 10 min, then (0.107 mL, 0.615 mmol) DIPEA was added. The reaction was stirred for 20 min at 0° C., and then for a further 3 h while warming to rt. The mixture was diluted with EtOAC (25 mL) and washed with 1N HCl, saturated $NaHCO_3$ solution and saturated NaCl solution. The organic layer was dried over $Na_2SO_4$, filtered and concentrated under reduced pressure. The crude product was purified by flash chromatography (0%-100% EtOAc in hexanes) and EuK-IPPA·3OtBu (10) was isolated as a yellow oil (167 mg, 74%). $^1$H NMR (500 MHz, $CDCl_3$) δ 7.51 (d, 2H, J=8.4 Hz), 7.09 (br s, 1H), 6.98 (d, 2H, J=8.4 Hz), 6.00 (d, 1H, J=8.4 Hz), 5.70 (d, 1H, J=7.9 Hz), 4.25 (m, 1H), 4.10 (m, 1H), 3.41 (d, 2H, J=5.4 Hz), 3.13-3.07 (m, 2H), 2.23 (m, 2H), 1.97 (m, 1H), 1.76 (m, 1H), 1.61 (m, 1H), 1.41-1.23 (m, 3H), 1.37 (s, 9H), 1.33 (s, 18H), 1.21 (m, 2H) ESI(+)=722.4 [M+H]$^+$. Calculated mass: 721.3.

EuK-IPAA·3OtBu (10) (114 mg, 159 μmol) was dissolved in $CH_2Cl_2$ (0.5 mL) and TFA (0.5 mL) and stirred at rt under Ar for 5 h. The solvent was removed under a stream of $N_2$ and the crude product was purified by prep HPLC. The peak corresponding to the product was collected and lyophilized, and RPS-027 was isolated as a white solid residue (85 mg, 95%). $^1$H NMR (500 MHz, DMSO) δ 12.44 (br s, 3H), 8.05 (t, 1H, J=5.5 Hz), 7.66 (d, 2H, J=8.4 Hz), 7.07 (d, 2H, J=8.4 Hz), 6.35 (d, 1H, J=8.3 Hz), 6.31 (d, 1H, J=8.3 Hz), 4.14-4.05 (m, 2H), 3.36 (s, 2H), 3.03 (m, 2H), 2.33-2.21 (m, 2H), 1.95 (m, 1H), 1.63-1.57 (m, 2H), 1.49 (m, 1H), 1.41 (m, 2H), 1.30 (m, 211). ESI(+)=563.9 [M+H]$^+$; 561.9 [M−H]$^-$. Calculated mass: 563.1.

Di-tert-butyl (((S)-1-(tert-butoxy)-1-oxo-6-(4-(4-(trimethylstannyl)phenyl)butanamido)hexan-2-yl)carbamoyl)-L-glutamate (11)

To a solution of EuK-IPBA·3OtBu (4) (86 mg, 113 μmol) in dioxane (20 mL) was added $(SnMe_3)_2$ (92.7 mg, 283 μmol) and $PdCl_2(PPh_3)_2$ (8 mg, 11.3 μmol), and the mixture was heated to 80° C. under Ar for 90 min. Then it was cooled to room temperature and the solvent was removed under reduced pressure. The crude residue was dissolved in $CH_2Cl_2$ (25 mL) and filtered through celite. The filtrate was concentrated under reduced pressure and the crude residue was purified by flash chromatography (0%-100% EtOAc in hexanes). The product EuK-IPBA.$SnMe_3$ (11) was isolated as a clear oil that solidified upon standing (18 mg; 20%), $^1$H NMR (500 MHz, DMSO) δ 7.75 (m, 1H), 7.34 (d, 2H, J=7.4 Hz), 7.13 (d, 2H, J=7.6 Hz), 6.27 (m, 2H), 4.03 (m, 1H), 3.95 (m, 1H), 3.00 (m, 2H), 2.52 (2H), 2.22 (m, 2H), 2.04 (t, 2H, J=7.4 Hz), 1.85 (m, 1H), 1.76 (quint, 2H, J=7.4 Hz), 1.67 (m, 1H), 1.58 (m, 1H), 1.50 (m, 1H), 1.38 (s, 27H), 1.32 (m, 2H), 1.26 (m, 2H), 0.24 (s, 9H). ESI(+)=798.1 (100%), 796.2 (75%), 794.2 (45%) [M+H]$^+$. Calculated mass: 797.4 (100%), 795.4 (74.3%), 793.4 (44.6%).

Di-tert-butyl (((S)-1-(tert-butoxy)-1-oxo-5-(4-(4-(trimethylstannyl)phenyl)butanamido)pentan-2-yl)carbamoyl)-L-glutamate (12)

To a solution of EuO-IPBA·3OtBu (5) (74 mg, 9.9 μmol) in dioxane (3 mL) was added $(SnMe_3)_2$ (52 μL, 25.0 μmol) and $PdCl_2(PPh_3)_2$ (7 mg, 10.0 μmol), and the resulting mixture was heated to 80° C. under Ar for 90 min. The reaction was then cooled to rt and the solvent was concentrated under reduced pressure. The crude residue was dissolved in $CH_2Cl_2$ (20 mL) and filtered through celite. The filtrate was concentrated under reduced pressure to give a brown oil. The oil was purified by silica chromatography (50%-90% EtOAc in hexanes) and a colorless oil was isolated from which a white solid precipitated. The oil was re-dissolved in $CH_2Cl_2$, filtered and concentrated under reduced pressure to give EuO-IPBA.$SnMe_3$ (12) as a colorless oil (29 mg, 37%), 41 NMR (500 MHz, DMSO) δ 7.80 9 m, 1H), 7.37 (d, 2H, J=7.9 Hz), 7.14 (d, 2H, J=8.1 Hz), 6.32 (d, 1H, J=7.6 Hz), 6.24 (d, 1H, J=7.6 Hz), 4.03 (m, 1H), 3.96 (m, 1H), 3.03 (m, 2H), 2.52 (m, 2H), 2.18 (m, 2H), 2.07 (t, 2H, J=8.0 Hz), 1.86 (m, 1H), 1.77 (m, 2H), 1.66 (m, 1H), 1.59 (m, 1H), 1.50 (m, 1H), 1.38 (s, 9H), 1.32 (m, 2H), 0.24 (s, 9H). ESI(+)=784.4 (100%), 782.4 (70%), 780.3 (40%) [M+H]$^+$. Calculated mass: 783.4 (100%), 781.4 (74.3%), 779.4 (44.6%).

Di-tert-butyl (((S)-(1-tert-butoxy)-1-oxo-5-(3-(4-(trimethylstannyl)phenyl)propanamido)pentan-2-yl)carbamoyl)-L-glutamate (13)

To a solution of EuO-IPPA·3OtBu (6) (38 mg, 52 μmol) in dioxane (3 mL) was added $(SnMe_3)_2$ (43 mg, 130 μmol) and $PdCl_2(PPh_3)_2$ (3.7 mg, 5.2 μmol), and the reaction was heated to 80° C. for 100 min under Ar. The reaction was then cooled to rt and the solvent removed under reduced pressure. The crude residue was dissolved in $CH_2Cl_2$ (12 mL) and filtered through celite. The filtrate was concentrated under reduced pressure to give a brown oil. The oil was purified by silica chromatography (50% EtOAc in hexanes) to give EuO-IPPA.$SnMe_3$ (13) as a colorless oil that solidified upon standing (15 mg; 38%). $^1$H NMR (500 MHz, $CDCl_3$) δ 7.41 (d, 2H, J=7.9 Hz), 7.20 (dd, 2H, $J_1$=12.8 Hz, $J_2$=4.9 Hz), 6.24 (t, 1H, J=5.5 Hz), 5.27 (d, 2H, J=8.1 Hz), 4.36-4.28 (m, 2H), 3.31 (m, 1H), 3.20 (m, 1H), 2.94 (t, 2H, J=7.9 Hz), 2.48 (t, 2H, J=8.0 Hz), 2.25 (m, 2H), 2.08 (m, 1H), 1.85 (m, 1H), 1.74 (m, 1H), 1.59-1.46 (m, 3H), 1.45 (s, 18H), 1.44 (s, 9H), 0.27 (s, 9H). ESI(+)=770.3 (100%), 768.2 (75%), 766.4 (50%) [M+H]$^+$. Calculated mass: 769.3 (100%), 767.3 (74.3%), 765.3 (44.6%).

Di-tert-butyl (((S)-1-tert-butoxy)-1-oxo-5-(2-(4-(trimethylstannyl)phenyl)acetamido)pentan-2-yl)carbamoyl)-L-glutamate (14)

EuO-IPAA·3OtBu (7) (22 mg, 31 μmol) was dissolved in dioxane (5 mL). $(SnMe_3)_2$ (16 μL, 77 μmol) and $PdCl_2(PPh_3)_2$ (2.2 mg, 5.1 μmol) were added consecutively and the reaction was heated to 80° C. for 3 h under Ar. It was then cooled to rt and filtered through celite. The celite was washed with dioxane (6 mL) and $CH_2Cl_2$ (5 mL). The combined organic fractions were concentrated under reduced pressure to give a pale oil. The oil was purified by silica chromatography (0%-90% EtOAC in hexanes), and the product v/as collected and lyophilized to give EuO-IPAA.$SnMe_3$ (14) as a white solid (8 mg; 35%). $^1$H NMR (500 MHz, $CDCl_3$) δ 8.06 (t, 1H, J=5.7 Hz), 7.39 (d, 2H, J=7.9 Hz), 7.21 (d, 2H, J=7.9 Hz), 6.31 (d, 1H, J=8.4 Hz), 6.26 (d, 1H, J=8.3 Hz), 4.04 (m, 1H), 3.98 (m, 1H), 3.31 (s, 2H), 3.02 (m, 2H), 2.29-2.19 (m, 3H), 1.87 (m, 1H), 1.67 (m, 1H), 1.63 (m, 1H), 1.50 (m, 2H), 1.40 (s, 9H), 1.39 (s, 9H), 1.38 (s, 9H), 0.25 (s, 9H). ESI(+)=756.2 (100%), 754.3 (70%), 752.4 (45%) [M+H]$^+$. Calculated mass: 755.3 (100%), 753.3 (74.3%), 751.3 (44.6%).

Tetra-tert-butyl (3S,7S,12S)-5,10,18-trioxo-21(4-(trimethylstannyl)phenyl)-4,6,11,17-tetraazahenicosane-1,3,7,12-tetracarboxylate (15)

EuEKIPBA·4OtBu (8) (25 mg, 26 μmol) and $PdCl_2(PPh_3)_2$ (2.1 mg, 3.0 μmol) were dissolved in dioxane (3 mL) and stirred at rt under Ar. Then $(SnMe_3)_2$ (25 mg, 75 μmol) was added and the reaction was heated to 80° C. and stirred under Ar for 90 min. The reaction was then cooled to rt and concentrated under reduced pressure. The crude residue was dissolved in $CH_2Cl_2$ (5 mL) and filtered through celite. The filtrate was concentrated and the residue was purified by silica chromatography (50%-100% EtOAc in hexanes), and EuEK-IPBA.$SnMe_3$ (15) was isolated as a clear oil (19 mg; 73%) that solidified upon standing at 0° C. $^1$H NMR (500 MHz, $CDCl_3$) δ 7.40 (d, 2H, J=7.9 Hz), 7.23 (d, 1H, J=7.7 Hz), 7.16 (dd, 2H, $J_1$=12.7 Hz, $J_2$=4.9 Hz), 5.90 (d, 1H, J=8.5 Hz), 5.75 (t, 1H, J=5.5 Hz), 5.25 (d, 1H, J=9.0 Hz), 4.46 (m, 1H), 4.36 (m, 1H), 4.23 (m, 1H), 3.22 (m, 2H), 2.62 (t, 2H, J=7.6 Hz), 2.33 (t, 2H, J=7.8 Hz), 2.28 (m, 1H), 2.20-2.15 (m, 5H), 2.04 (m, 1H), 2.00-1.91 (m, 3H), 1.73 (m, 2H), 1.65 (m, 2H), 1.47 (s, 9H), 1.46 (s, 9H), 1.45 (s, 9H), 1.43 (s, 9H), 1.40 (m, 2H), 0.27 (s, 9H). ESI(+)=983.8 (100%), 981.8 (75%), 984.9 (50%) [M+H]$^+$. Calculated mass: 982.5 (100%), 980.5 (74.3%) 983.5 (49.8%).

Di-tert-butyl (((S)-1-(tert-butoxy)-1-oxo-6-(3-(4-(trimethylstannyl)phenyl)propanamido)hexan-2-yl) carbamoyl)-L-glutamate (16)

To a solution of EuK-IPPA·3OtBu (9) (59 mg, 79 μmol) in dioxane (20 mL) was added $(SnMe_3)_2$ (65 mg, 198 μmol) and $PdCl_2(PPh_3)_2$ (5.6 mg, 7.9 μmol), and the mixture was heated to 80° C. under Ar for 90 min. Then it was cooled to room temperature and the solvent was removed under reduced pressure. The crude residue was dissolved in $CH_2Cl_2$ (25 mL) and filtered through celite. The filtrate was concentrated under reduced pressure and the crude residue was purified by flash chromatography (0%-100% EtOAc in hexanes). The product EuK-IPPA.$SnMe_3$ (16) was isolated as a clear oil that solidified upon standing (51 mg; 82%). $^1$H NMR (500 MHz, DMSO) δ 7.82 (m, 1H), 7.39 (d, 2H, J=8.0 Hz), 7.17 (d, 2H, J=8.1 Hz), 6.33 (d, 1H, J=5.9 Hz), 6.27 (d, 1H, J=6.1 Hz), 4.06 (m, 1H), 3.97 (m, 1H), 3.04 (m, 2H), 2.79 (t, 2H, J=7.7 Hz), 2.34 (t, 2H, J=7.8 Hz), 2.24 (m, 2H), 1.89 (m, 1H), 1.69 (m, 1H), 1.58 (m, 1H), 1.52 (m, 1H), 1.41 (s, 27H), 1.34 (m, 2H), 1.26 (m, 2H), 0.25 (s, 9H). (ESI(+)=784.2 (100%), 782.2 (75%), 780.3 (45%) [M+]$^+$. Calculated mass: 783.4 (100%), 781.4 (74.3%), 779.4 (44.6%).

Di-tert-butyl (((S)-1-(tert-butoxy)-1-oxo-6-(2-(4-(trimethylstannyl)phenyl)acetamido)hexan-2-yl) carbamoyl)-L-glutamate (17)

To a solution of EuK-IPAA·3OtBu (10) (70 mg, 96 μmol) in dioxane (20 mL) was added $(SnMe_3)_2$ (78 mg, 239 μmol) and $PdCl_2(PPh_3)_2$ (6.7 mg, 9.6 μmol), and the mixture was heated to 80° C. under Ar for 90 min. Then it was cooled to room temperature and the solvent was removed under reduced pressure. The crude residue was dissolved in $CH_2Cl_2$ (25 mL) and filtered through celite. The filtrate was concentrated under reduced pressure and the crude residue was purified by flash chromatography (0%-100% EtOAc in hexanes). The product EuK-IPAA.$SnMe_3$ (17) was isolated as a clear oil that solidified upon standing (50 mg; 69%). $^1$H NMR (500 MHz, $CDCl_3$) δ 7.41 (d, 2H, J=7.9 Hz), 7.23 (d, 2H, J=7.9 Hz), 6.39 (m, 1H), 5.70 (d, 1H, J=8.3 Hz), 5.55 (d, 1H, J=7.9 Hz), 4.32 (m, 1H), 4.21 (m, 1H), 3.51 (d, 2H, J=5.1 Hz), 3.21 (m, 1H), 3.10 (m, 1H), 2.22 (m, 2H), 2.02 (m, 1H), 1.84 (m, 1H), 1.66 (m, 1H), 1.49 (m, 1H), 1.42 (m, 2H), 1.41 (s, 9H), 1.40 (s, 9H), 1.39 (s, 9H), 1.30 (m, 2H), 0.24 (s, 9H). ESI(+) 770.1 (100%), 768.2 (75%), 766.0 (45%) [M+H]$^+$. Calculated mass: 769.3 (100%), 767.3 (74.3%), 765.3 (44.6%).

Radiosynthesis of Exemplary Compounds. A representative synthetic scheme for certain exemplary compounds of the present technology is presented below in Scheme 2.

Scheme 2.

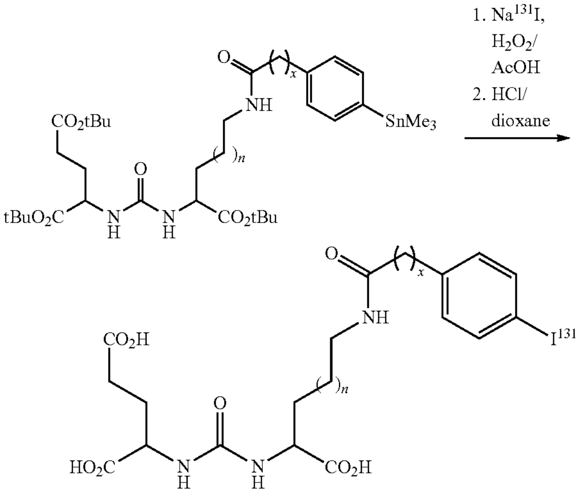

$^{131}$I-RPS-005: n = 2, x = 3
$^{131}$I-RPS-020: n = 1, x = 3
$^{131}$I-RPS-022: n = 1, x = 2
$^{131}$I-RPS-027: n = 2, x = 1

Radiolabeling was carried out according to a modified version of the protocol described in Zechmann C M, Afshar-Oromieh A, Armor T, et al. Radiation dosimetiy and first therapy results with a $^{124}I/^{131}I$-labeled small molecule (MIP-1095) targeting PSMA for prostate cancer therapy, *Eur J Nucl Med Mol Imaging.* 2014; 41:1280-1292, incorporated herein by reference. 100 μL of a 250 μg/mL solution of organnostannane precursor (e.g., any one of compounds 11-17) in EtOH was added to a vial containing 74-740 MBq (2-20 mCi) $Na^{124}I$ or $Na^{131}I$ in 30-60 μL aqueous NaOH. A 15% v/v $H_2O_2$/ACOH solution was prepared and 50 μL was transferred immediately to the reaction vial. The reaction was mixed for 20 s and let stand for 5 min at room temperature. It was then diluted with 3 mL $H_2O$ and passed through a pre-activated SOLA™ cartridge (Thermo Scientific). The cartridge was washed with $H_2O$ (3 mL) and dried with air. The radiolabeled intermediate was eluted into a second vial with 1 mL of a 4M HCl/dioxane solution. The reaction was mixed for 20 s and let stand for 40 min. It was then diluted with FLO (9 mL) and passed through a pre-activated Bond Eiut Plexa™ cartridge (Agilent Technologies, Inc.). The cartridge was washed with 5 mL of a 20% v/v $EtOH/H_2O$ solution and dried with air. The radiolabeled product was eluted with DMSO (100-300 μL).

The radiochemical yield, radiochemical purity, and specific activity are provided below in Table 1, where RCY=radiochemical yield, RCP=radiochemical purity, and S.A.=Specific activity.

TABLE 1

| Compound | RCY (%) | RCP (%) | S.A. (GBq/μmol)[1] |
|---|---|---|---|
| $^{131}$I-RPS-001 | 71.8 | >97 | 3.15 |
| $^{131}$I-RPS-005 | 62.0 | >96 | 3.52 |
| $^{131}$I-RPS-020 | 66.7 | >94 | 4.29 |
| $^{131}$I-RPS-022 | 53.6 | >90 | 3.06 |
| $^{131}$I-RPS-025 | 43.5 | >93 | 2.02 |
| $^{131}$I-RPS-027 | 49.5 | >98 | 9.18 |

[1]Based on a starting activity of 72-370 MBq (2-10 mCi)

Radiochemical yield ranged from 43-72% and radiochemical purity was greater than 90% for all compounds tested. For example, $^{131}$I-RPS-027 was prepared in 49.5% radiochemical yield from its organostannane precursor. Specific activity varied from 2-10 GBq/μmol according to the starting $^{124}$I or $^{131}$I activity. The deprotection step proved to be time sensitive: for reaction times below 40 minutes, incomplete deprotection was observed, while reaction times greater than 45 minutes led to the formation of an unidentified impurity that could not be removed during purification by solid phase extraction. No significant difference in labeling yield was observed when $^{124}$I was used in place of $^{131}$I. The structure for $^{131}$I-RPS-001 (alternately described herein as $^{131}$I-MIP-1095) is provided below.

$^{131}$I-PRS-001

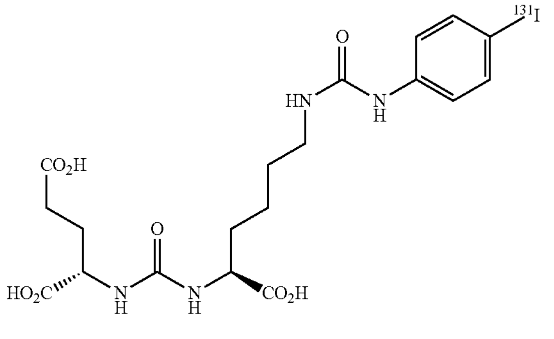

Representative Biological Assays

USA affinity determination. HSA was immobilized to HPLC-grade silica by the Schiff base method as described previously and were packed into 10 mm×2.1 mm i.d. microcolumns. See Chen J, Hage D S. Quantitative studies of allosteric effects by biointeraction chromatography: analysis of protein binding for low-solubility drugs. *Anal Chem.* 2006:78:2672-2683 and Matsuda R, Anguizola J, Hoy K S, Hage D S. Analysis of drug-protein interactions by high-performance affinity chromatography: interactions of sulfonyl urea drugs with normal and glycated human serum albumin. *Methods Mol Biol.* 2015; 1286:255-277, each of which is incorporated herein by reference. The protein content of these columns was approximately 60 mg HSA per gram of silica. See Zheng X, Podariu M, Bi C, Hage D S. Development of enhanced capacity affinity microcolumn by using a hybrid of protein cross-linking/modification and immobilization. *J. Chromatogr A.* 2015; 1400:82-90, incorporated herein by reference. Control microcolumns were prepared in the same manner but with no HSA being added during the immobilization step. The retention factor for each compound was measured on both an HSA microcolumn and a control column by injecting 5 μL samples that contained approximately 50 μM of the compound in 0.067M potassium phosphate buffer (pH 7.4). All samples were injected in triplicate at room temperature and at 1.0 mL/min, with the phosphate buffer used as the mobile phase. Similar injections were made with samples containing sodium nitrate, which was used as a void volume marker. Elution of the injected compounds was monitored by absorbance detection. The dissociation constant (Kd) for each compound with HSA estimated by using the measured retention factors, after correcting for any-observed retention on the control column, along with the estimated content of active HSA in the column, as based on injections made with warfarin and L-tryptophan (i.e., probes for Sudlow sites I and II of HSA). See Chen J, Hage D S. *Anal Chem.* 2006:78:2672-2683 (cited above) and Joseph K S, Hage D S. The effects of glycation on the binding of human serum albumin to warfarin and L-tryptophan. *J Pharm Biomed Anal.* 2010; 53:811-818, incorporated herein by reference. The estimated precision of the Kd values was ±2-14%.

Cell Culture. The PSMA-expressing human prostate cancer cell line, LNCaP, was obtained from the American Type Culture Collection. Cell culture supplies were from Invitrogen unless otherwise noted. LNCaP cells were maintained in RPMI-1640 medium supplemented with 10% fetal bovine serum (Hyc-lone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 μg/mL gentamicin in a humidified incubator at 37° C./5% $CO_2$. Cells were removed from flasks for passage or for transfer to 12-well assay plates by incubating them with 0.25% trypsin/ethylenediaminetetraacetic acid (EDTA).

In vitro determination of $IC_{50}$. $IC_{50}$ values of the non-radioactive iodine-containing ligands were determined by screening in a multi-concentration competitive binding assay against $^{99m}$Tc-((7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid technetium tricarbonyl complex) ($^{99m}$Tc-MIP-1427) for binding to PSMA on LNCaP cells, according to protocols described in Kelly J, Amor-Coarasa A, Nikolopoulou A, et al. Synthesis and pre-clinical evaluation of a new class of high-affinity $^{18}$F-labeled PSMA ligands for detection of prostate cancer by PET imaging. Eur J Nucl Med Mol Imaging. 2017; 44, 647-661, incorporated herein by reference. Briefly, LNCaP cells were plated 48 h prior to the experiment to achieve a density of approximately $5\times10^3$ cells/well (in triplicate) in RPMI-1640 medium supplemented with 0.25% bovine serum albumin. The cells were incubated for 1 h with 1 nM $^{99m}$Tc-MIP-1427 in serum-free RPMI-1640 medium in the presence of 0.1-10,000 nM test compounds. Radioactive incubation media was then removed by pipette and the cells were washed twice using 1 mL ice-cold HEPES buffer. Cells were harvested from the plates and transferred to tubes for radioactive counting using a Packard Cobra II Gamma Counter. $IC_{50}$ values were determined by non-linear regression using GraphPad Prism software.

Inoculation of mice with xenografts. All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Male inbred athymic nu/nu mice were purchased from The Jackson Laboratory. For inoculation in mice, LNCaP cells were suspended at $4\times10^7$ cells/mL in a 1:1 mixture of PBS:Matrigel (BD Biosciences). Each mouse was injected in the left flank with 0.25 mL of the cell suspension. The mice were imaged when the tumors reached approximately 200-400 $mm^3$, while biodistributions were conducted when tumors were in the range 100-400 $mm^3$.

Tissue Distribution Studies. A quantitative analysis of the tissue distribution of $^{131}$I labeled compounds was performed in separate groups of male NCr-nu/nu mice bearing LNCaP ceil xenografts administered via the tail vein as a bolus injection (approximately 370 kBq (10 μCi)/mouse) in a volume of 0.05-0.1 mL of saline solution containing 2.5% v/v DMSO. The animals (n=3-5/time point) were euthanized by asphyxiation with $CO_2$ at the indicated time points after injection. Tissues, including blood, heart, lungs, liver, spleen, pancreas, kidneys, stomach, large and small intestines (with contents), skeletal muscle, bone, and tumor, were dissected, excised, weighed wet (Sartorius analytical balance), and counted in a Wizard automated γ-counter (Perkin Elmer). A 1% ID/g standard was counted with the tissue samples. Tissue time-radioactivity levels expressed as percent injected dose per gram of tissue (% ID/g) were determined. Blood pharmacokinetics were modeled as a dual compartment system using bi-exponential least-squares regression fit to the data. Regression method was implemented in MATLAB R2015b (MathWorks, Natick, MA).

Imaging Studies. LNCaP xenograft tumor-bearing mice (two per compound) were injected intravenously via the tail vein as a bolus injection of 7.03-7.77 MBq (190-210 μCi) of $^{124}$I-RPS-027. The specific activity of $^{124}$I-RPS-027 was in the range 3-10 GBq/μmol. The mice were imaged by μPET/CT (Inveon™; Siemens Medical Solutions, Inc.) at 1 h, 3 h, 6 h, 24 h and 48 h post-injection. Total acquisition time was thirty minutes, and a CT scan was obtained either immediately before or immediately after the acquisition for both anatomical co-registration and attenuation correction. The data were reconstructed using the commercial Inveon™ software supplied by the vendor. Image-derived tumor uptake was estimated by drawing a region of interest (ROI).

Representative Activity of Compounds of the Present Technology

Exemplary In Vitro Study Results.

Table 2 below provides the results of the affinity studies for certain exemplary compounds with PMSA and human serum albumin ("HSA").

TABLE 2

| Compound | $IC_{50}$ for PSMA (nM) | Kd for HSA (μM) |
|---|---|---|
| RPS-001 (MIP-1095) | 0.3 | 19.2 |
| RPS-005 | 4 | 0.98 |
| RPS-020 | 8 | 2.1 |
| RPS-022 | 10 | 22.9 |
| RPS-023 | 10 | 53.2 |
| RPS-025 | 15 | <1* |
| RPS-026 | 40 | 26.6 |
| RPS-027 | 15 | 11.2 |

*Note:
RPS-025 could not be eluted from the HSA affinity microcolumn, which prevented the calculation of a precise Kd The range of affinities for PSMA was determined to be 4-40 nM, with the majority of the compounds clustered between 10 nM and 15 nM. In the same assay, RPS-001 (also known as MIP-1095) was found to have an $IC_{50}$ of 0.3 nM. Compounds bearing the p-(iodophenyl)butyric acid moiety were found to have a high affinity (1-2 μM) for HSA. RPS-025 could not be eluted from the column, which prevented the calculation of a precise Kd. RPS-027 had a modest affinity of 11 μM, while RPS-001, RPS-022 and RPS-026 were in the range 19-26 μM. RPS-023 (Kd=53.2 μM) was determined to have a relatively weak affinity.

Biodistribution and μPET/CT Imaging In Vivo.

The biodistribution studies of the six ligands demonstrated that albumin binding affinity contributed markedly to the different pharmacokinetics observed in mice. RPS-001 (Kd=20 μM for HSA) demonstrated relatively rapid clearance from the blood (FIG. 1A). Initial kidney uptake was high (>100% ID/g) and from 24-96 h post injection, $^{131}$I-RPS-001 activity in the kidney cleared from 65.24±22.61% ID/g at 24 h to 2.12±2.47% ID/g at 96 h. Tumor uptake was high with gradual tumor washout observed over several days (19.81±6.16% ID/g at 24 h vs. 10.21±4.30% ID/g at 96 h) (FIG. 1A), such that tumor-to-kidney ratio increased with time. Low, PSMA-mediated uptake was observed at 24 h post injection in the large intestine (2.35±1.26% ID/g) and the spleen (2.41±1.40% ID/g), and accumulated activity was negligible in all tissues except for the tumor and kidney by 48 h post injection. The tissue uptake at earlier time points was extrapolated using previously reported data (37).

Figure 1B:
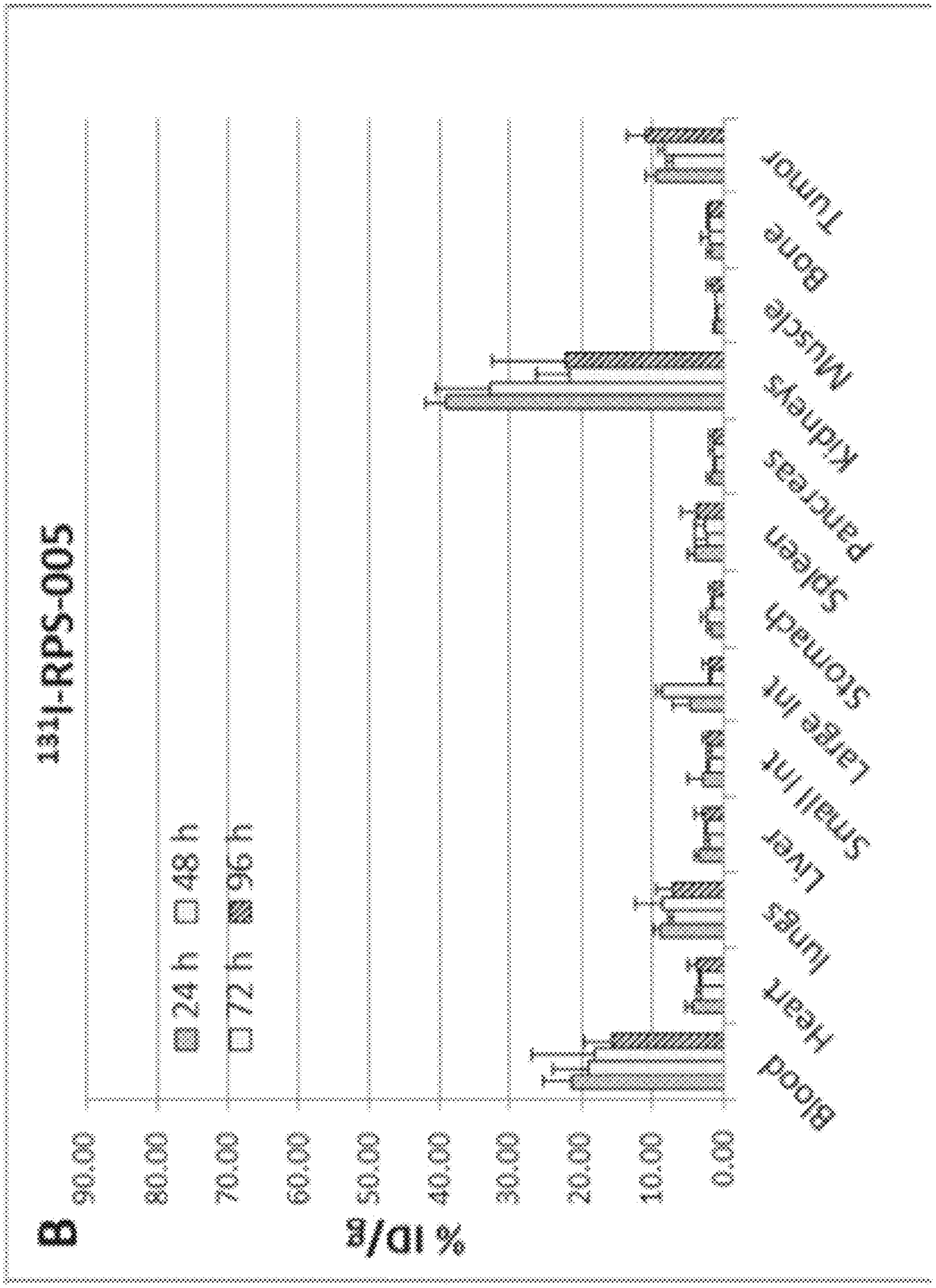

Accumulation of $^{131}$I-RPS-005 (Kd=0.89 μM for HSA) in the blood was exceptionally high, and clearance was slow over the 96 h observation window (FIG. 1B). At 24 h post injection, blood activity was 21.35±3.99% ID/g, which decreased to 15.57±3.98% E)/g by 96 h. This slow blood clearance is likely to be responsible for the non-PSMA-mediated uptake observed in tissues such as the heart (4.40±0.74% ID/g at 24 h), lungs (8.87±0.74% ID/g at 24 h) and liver (3.41±0.56% ID/g at 24 h). Kidney uptake (39.09±2.96% ID/g) was lower at 24 h post injection than observed for $^{131}$I-RPS-001, but clearance was considerably slower. In combination with the comparatively low tumor uptake of approximately 10% (9.37±1.56% ID/g at 24 h; 10.82±2.64% ID/g at 96 h), these pharmacokinetics result in poor tumor-to-background ratios at all time points.

Figure 2:
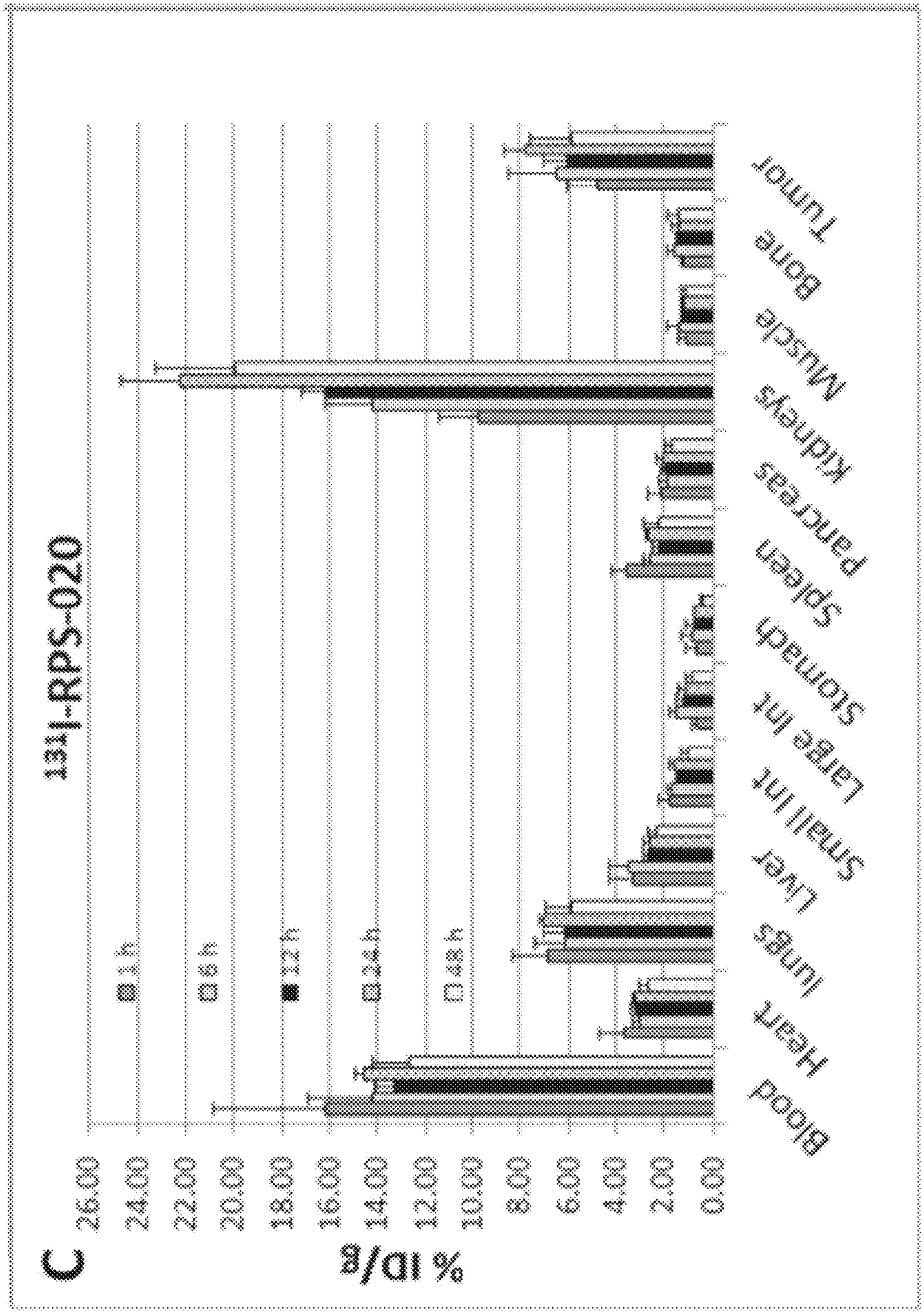
FIG. 2 provides the biodistribution of $^{131}$I-RPS-020 at 1, 6, 12, 24 and 48 h p.i. in male nude mice bearing PSMA+ LNCaP human tumor xenografts.

As the tissue uptake of $^{131}$I-RPS-005 appeared to peak within the first 24 h, $^{131}$I-RPS-020 (Kd=2.1 μM) was investigated at early time points as well. Prolonged blood retention was also observed, with initial accumulation of 16.20±4.68% ID/g at 1 h post injection only decreasing to 12.71±1.55% ID/g at 48 h (FIG. 2). This was associated with high off-target uptake, most notably in the lungs (6.12±0.95% ID/g at 1 h post injection) and kidneys (16.21±0.97% ID/g at 1 h). Activity continued to accumulate in the kidney, peaking at 22.26±2.48% ID/g at 24 h post injection. Tumor uptake (4.81±1.27% ID/g) was lower than observed for RPS-005, as a comparison of PSMA affinities might predict, but it remained stable over the course of the 48 h.

Figure 3:
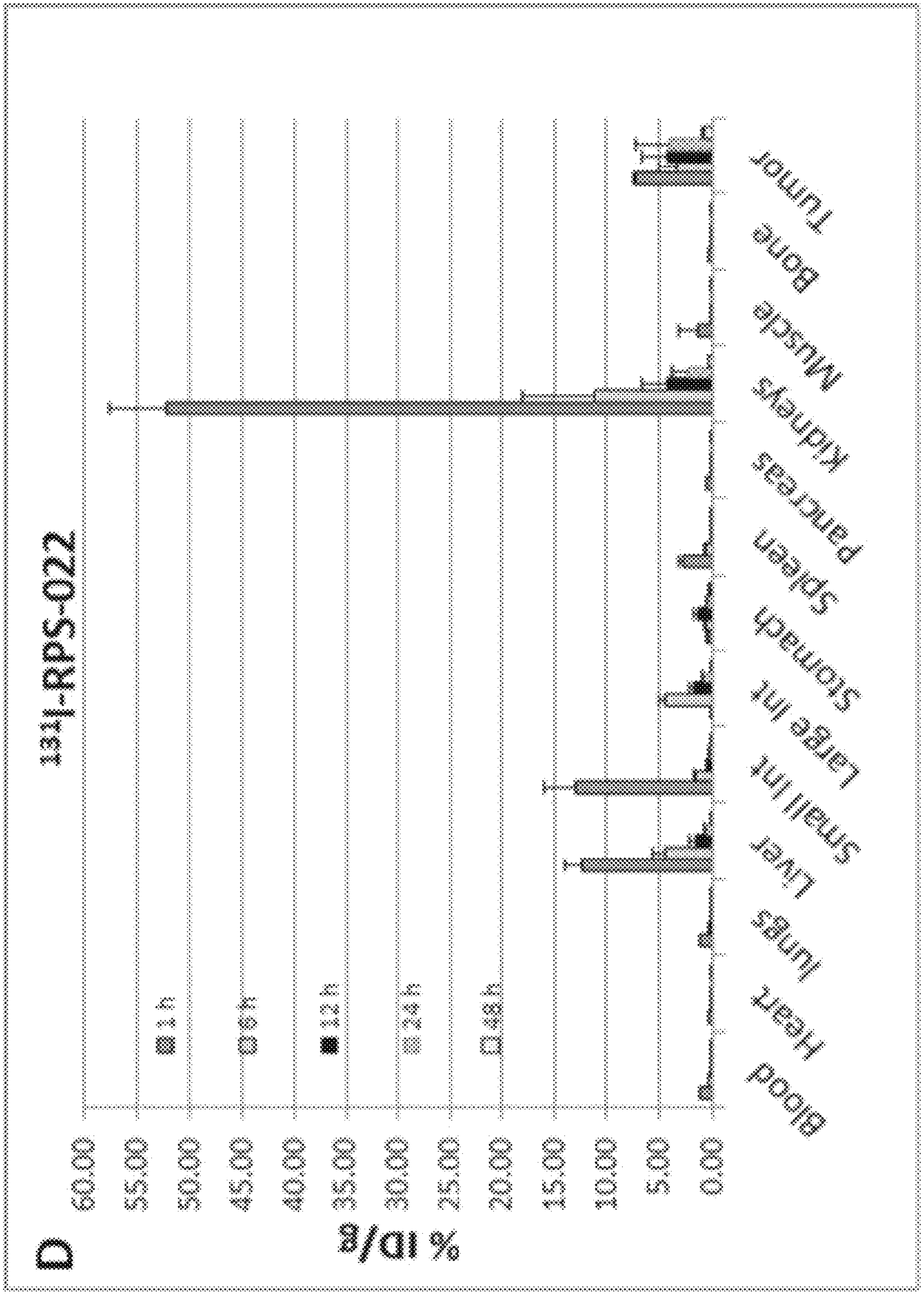
FIG. 3 provides the biodistribution of $^{131}$I-RPS-022 at 1, 6, 12, 24 and 48 h p.i. in male nude mice bearing PSMA+ LNCaP human tumor xenografts.

In contrast, $^{131}$I-RPS-022 (Kd=22.9 μM) showed rapid blood kinetics, with negligible activity detected as early as 12 h post injection (FIG. 3). Considerable uptake was observed in the liver (12.46±1.63% ID/g) and small intestine (13.09±2.98% ID/g) at 1 h post injection, though clearance from each organ was rapid. Kidney uptake, which reached (52.18±5.35% ID/g) at 1 h post injection, had cleared to 2.27±1.41% ID/g by 24 h, leading to favorable tumor-to-kidney and tumor-to-background ratios at later time points. However, tumor uptake peaked at 7.20±0.10% ID/g at 1 h post injection and subsequently decreased to 3.35±1.70% ID/g by 6 h.

Figure 4:
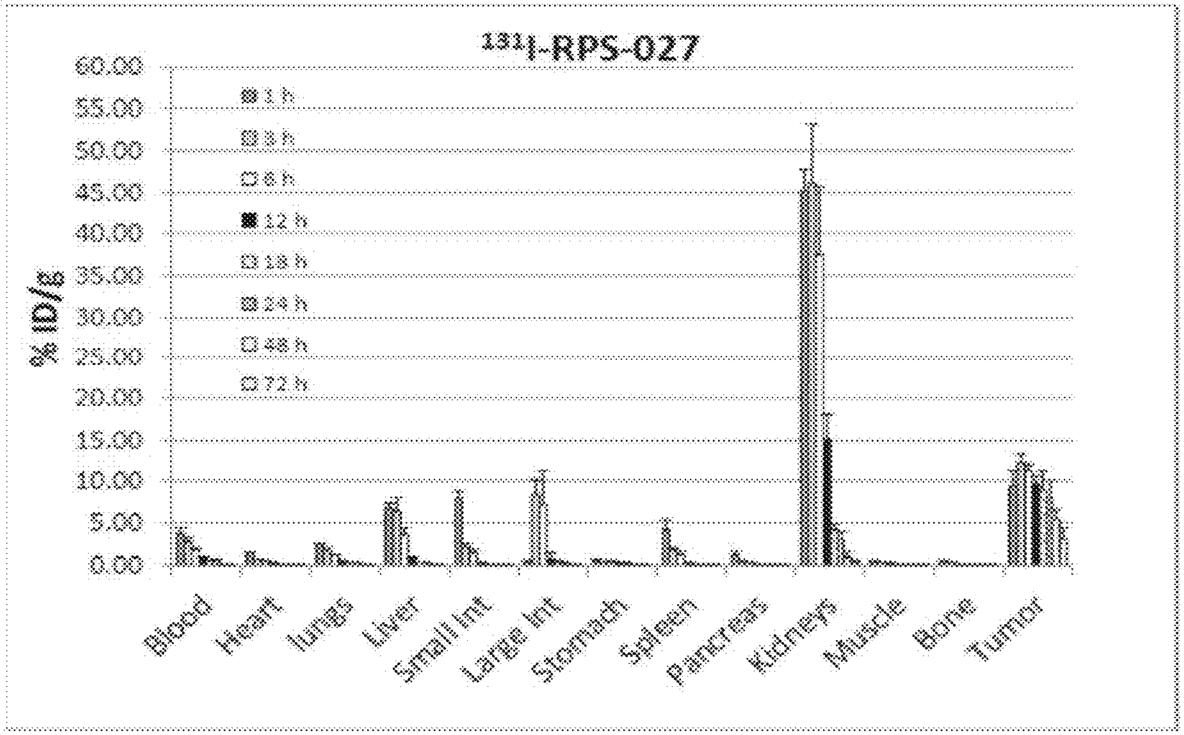
FIG. 4 provides the biodistribution of $^{131}$I-RPS-027 at 1, 3, 6, 12, 18, 24, 48, and 72 h p.i. in male nude mice bearing PSMA+LNCaP human tumor xenografts.

$^{131}$I-RPS-027 showed a promising biodistribution profile over the time period studied (FIG. 4). Activity in the blood at 1 h post injection was 3.91±0.48% ID/g, which decreased to 0.58±0.17% ID/g by 24 h. Initial uptake was also observed in the liver (6.79±0.70% ID/g; 1 h), small intestine (8.01±0.78% H)/g; 1 h), large intestine (8.56±1.67% ID/g; 3 h), spleen (4.13±1.37% ID/g; 1 h) and heart (1.30±0.04% ID/g; 1 h). Clearance from these tissues decreased largely in proportion to blood clearance, suggesting that the normal organ activity is related to blood pool activity rather than tissue uptake. Minimal activity was detected in the tissue by 12 h post injection with the exception of the kidney (15.12±2.82% ID/g) and the tumor (9.73±1.01% ID/g). Although maximum tumor uptake (12.41±0.84% ID/g, 3 h) was lower than for $^{131}$I-RPS-001, tumor uptake remained as high as 8.13±2.03% ID/g at 24 h and 3.05±1.30% ID/g at 72 h, leading to excellent tumor-to-background and tumor-to-kidney (>2) ratios as early as 18 h post injection. While tumor uptake of $^{131}$I-RPS-027 was roughly 50% of that for $^{131}$I-RPS-001 at all time points studied, the kidney concentration of $^{131}$I-RPS-027 was fivefold less than that for $^{131}$I-RPS-001.

Figure 5:
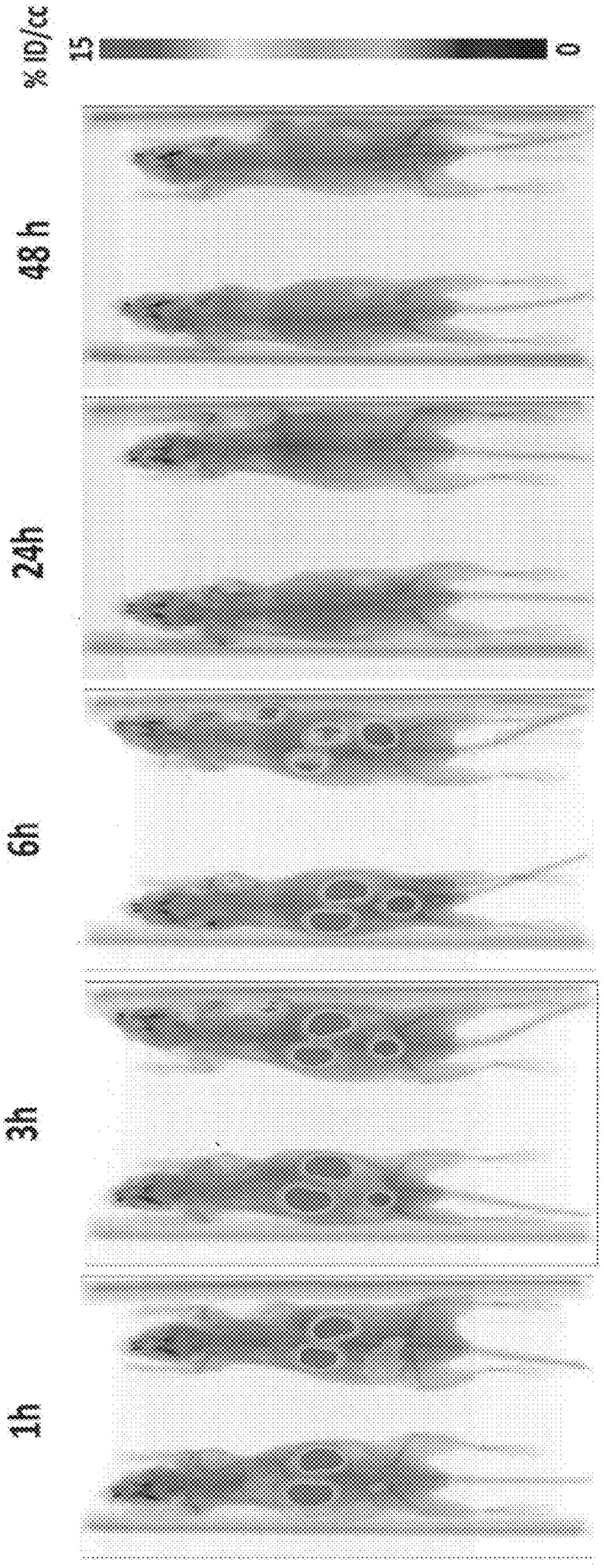
FIG. 5 provides the results of μPET/CT imaging of LNCaP xenograft mice by μPET/CT using $^{124}$I-RPS-027 (7.4 MBq, 200 μCi).

Desirable pharmacokinetics continued to be observed at longer time points for $^{131}$I-RPS-027 (FIG. 4), Activity in the blood remained detectable up to 48 h post injection (0.20±0.06% ID/g), while tumor-to-background ratio continued to increase due to rapid clearance from the kidney (1.04±0.65% ID/g at 48 h). These in vivo findings were visually recapitulated by μPET/CT imaging of LNCaP xenograft mice using $^{124}$I-RPS-027. Initial uptake in the tumor, kidneys and hepatobiliary system is evident at 1 h (FIG. 5), with clearance from non-target tissue resulting in highly specific tumor targeting at 24 h and 48 h post injection.

Figure 6A:
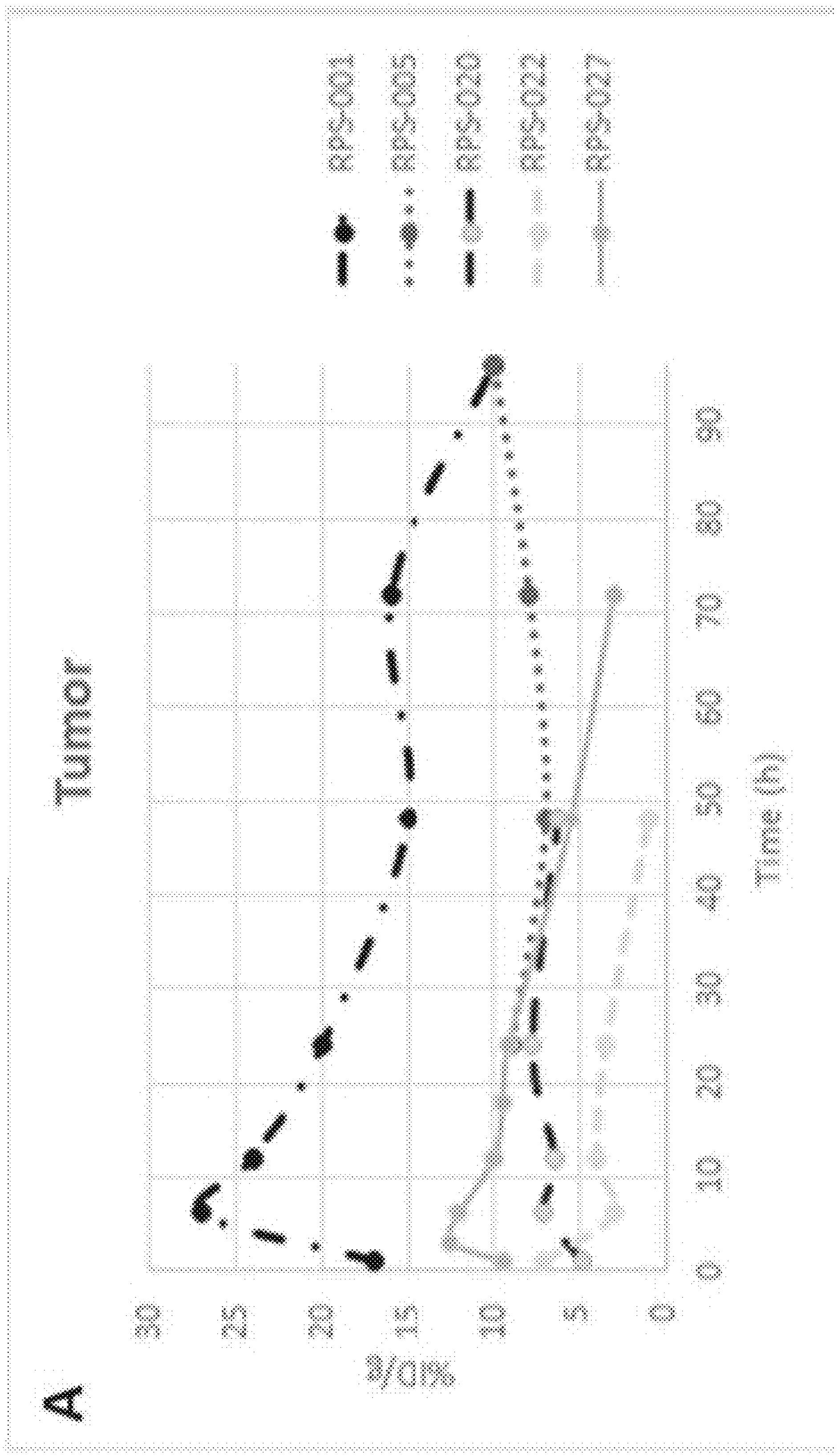
FIGS. 6A-6C are plots of time-activity curves for blood (FIG. 6A), tumor (FIG. 6B), and kidney (FIG. 6C) derived from biodistribution data.
Figure 6B:
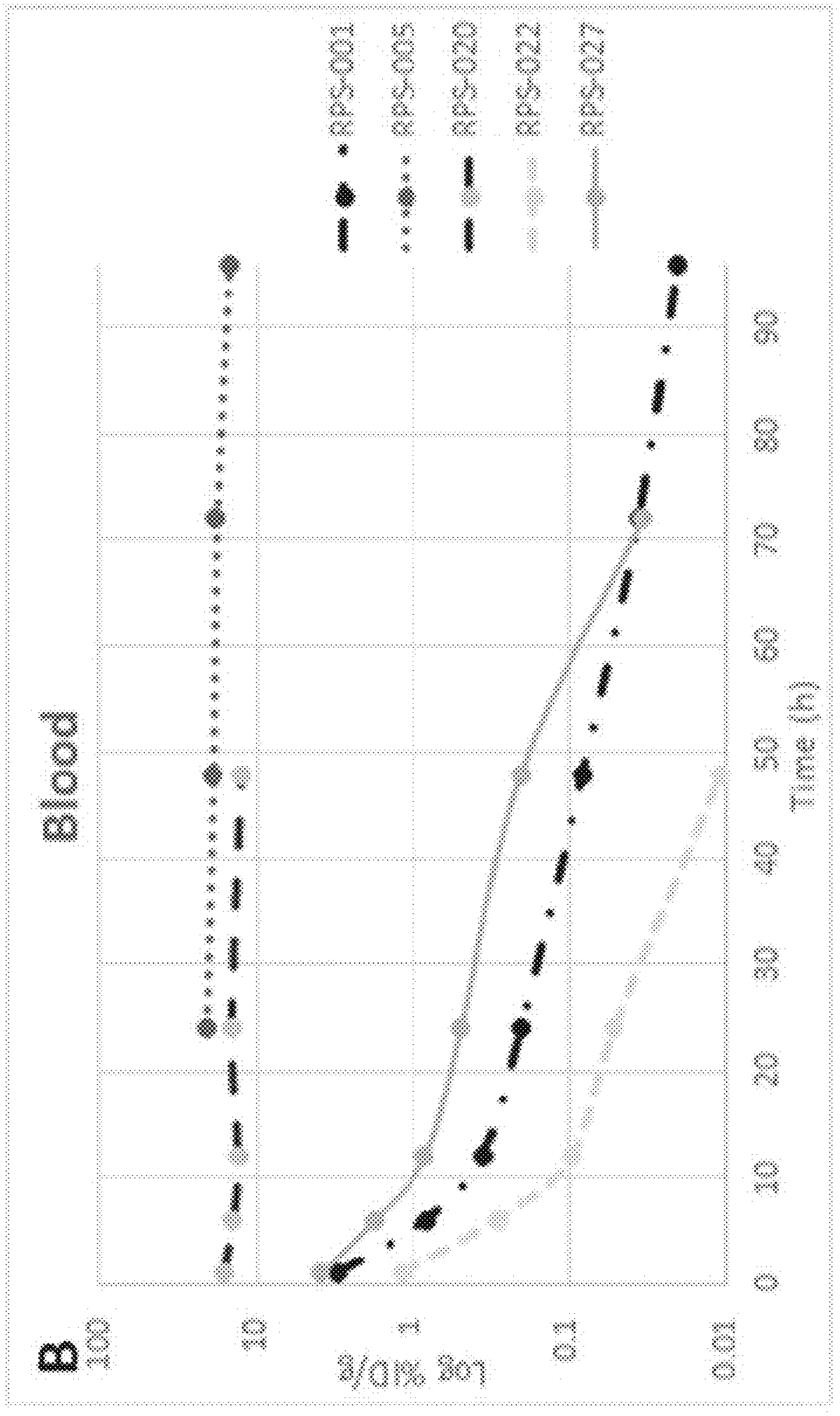

Time-activity curves were plotted to facilitate a greater understanding of the pharmacokinetic profile of the dual binding ligands. Uptake in the tumor, the blood and the kidneys is plotted in FIGS. 6A-6C. The highest tumor uptake is observed for $^{131}$I-RPS-001, and the kinetics of tumor washout are similar for the three compounds with lower affinity for albumin (FIG. 6A). The level of activity in the tumor remains most steady in the two ligands with highest albumin binding (FIG. 6A). Striking differences are apparent in the rate of blood clearance among the various compounds studied, with $^{131}$I-RPS-005 and $^{131}$I-RPS-020, both having high affinity for albumin, showing minimal blood clearance over 48 h and beyond (FIG. 6B). The clearance kinetics of $^{131}$I-RPS-001, $^{131}$I-RPS-022 and $^{131}$I-RPS-027 reflect their relative affinities for albumin, with $^{131}$I-RPS-022 clearing most quickly and $^{131}$I-RPS-027 clearing most gradually. Blood curves show a rapid initial distribution phase followed by a slower elimination phase. In this model, $t_{1/2}$ for the distribution phase was 2.17 h, 2.1 h and 3.15 h for $^{131}$I-RPS-001, $^{131}$I-RPS-022 and $^{131}$I-RPS-027, respectively, while the corresponding $t_{1/2}$ for the elimination phase was 20.38 h, 17.3 h and 21.66 h. In comparison, the half-lives for distribution and elimination phases for $^{131}$I-RPS-020 were 3.85 h and 3,300 h, respectively.

Figure 6C:
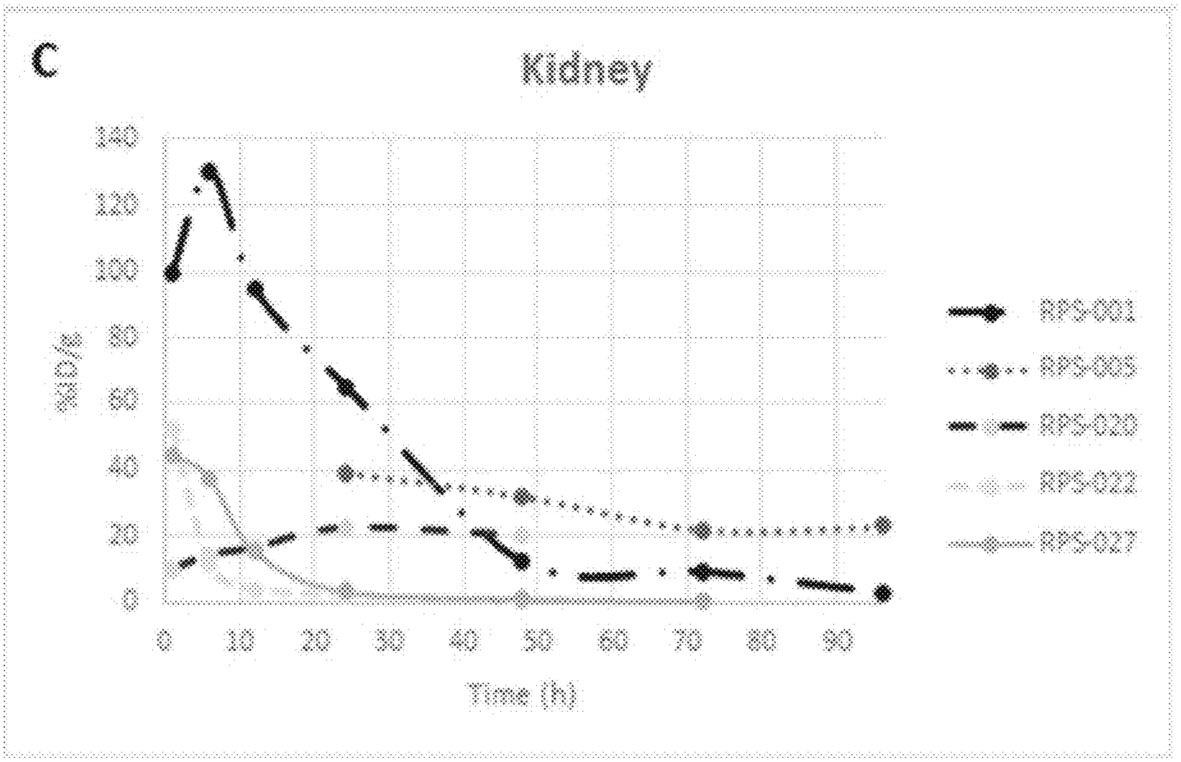
Figure 7A:
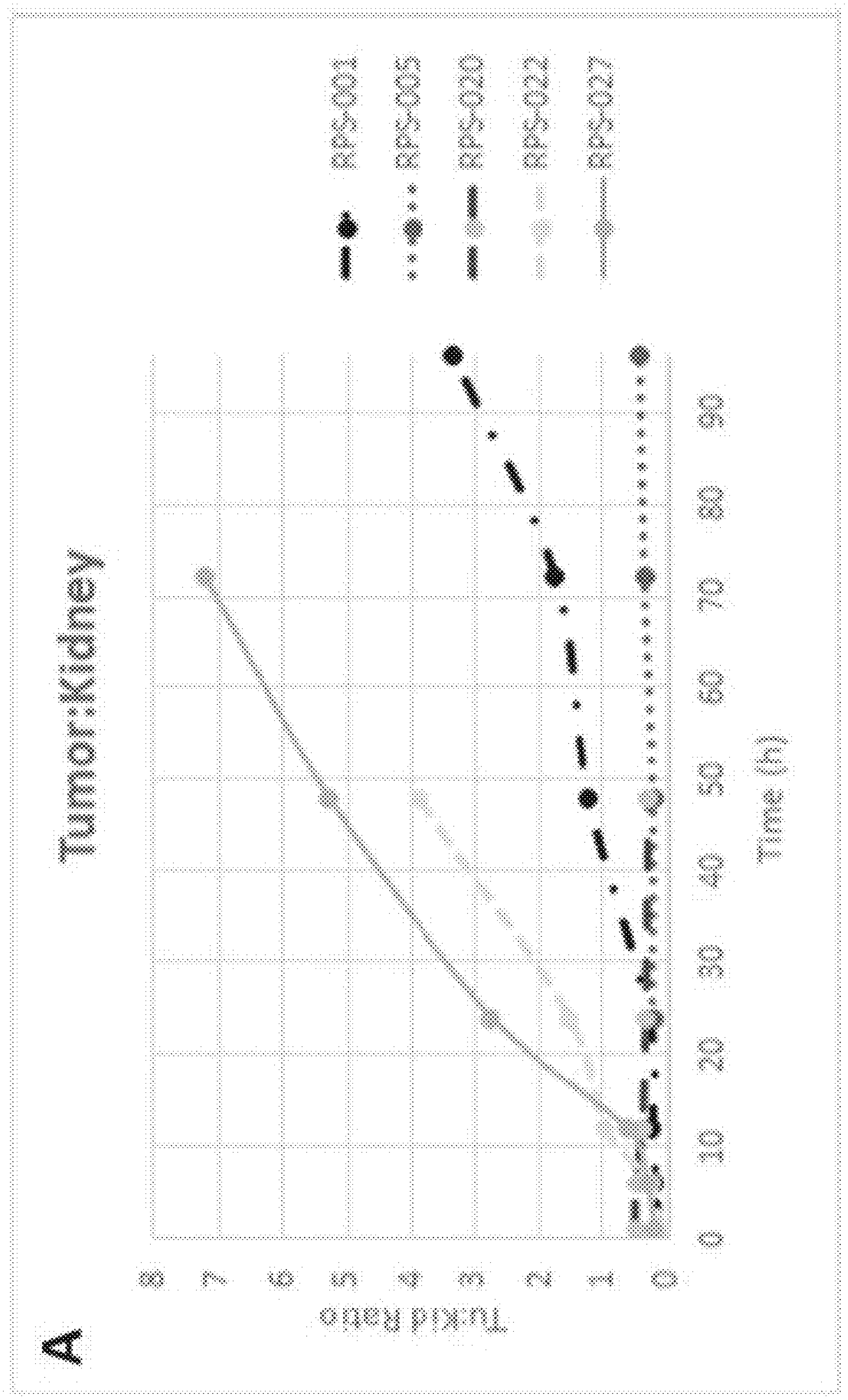
FIGS. 7A-7B provide the relative tumor-to-background ratios for tumor-to-blood (FIG. 7A) and tumor-to-kidney (FIG. 7B) further illustrating the effect of enhanced albumin-binding in tumor delivery of the respective compounds.
Figure 7B:
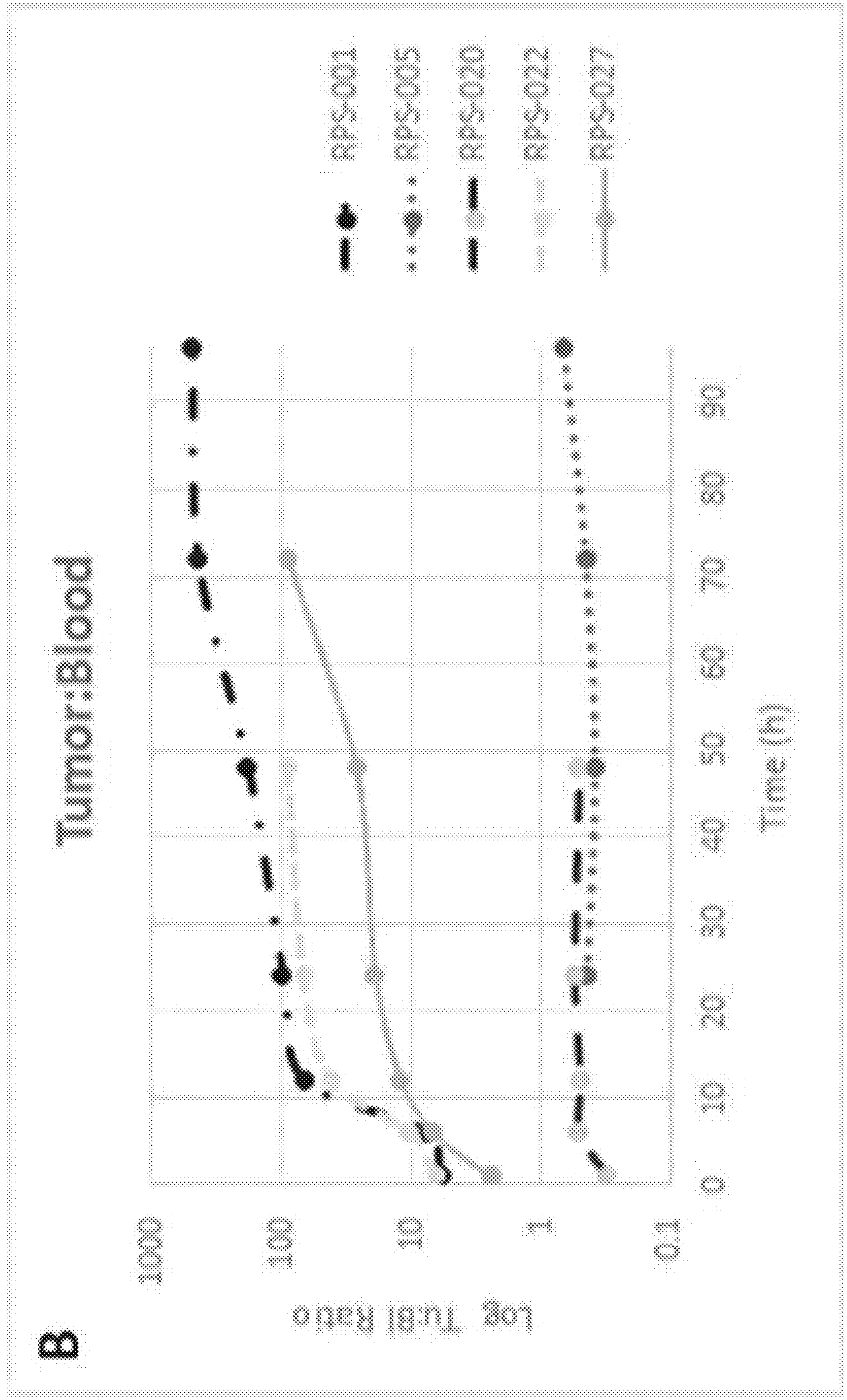

Absolute kidney uptake of RPS-027 and RPS-022 was dramatically reduced compared with RPS-001 at all time points studied. Kidney clearance is approximately described by an exponential decay function for $^{131}$I-RPS-001, $^{131}$I-RPS-022 and $^{131}$I-RPS-027 (FIG. 6C). In contrast, $^{131}$I-RPS-005 and $^{131}$I-020 show prolonged retention and much flatter clearance curves. Tumor-to-kidney (T/K) and tumor-to-blood (T/B) ratios were calculated as a function of time. The T/K ratio of $^{131}$I-RPS-027 reaches approximately 3 by 24 h and continues to increase with time (FIG. 7A). In comparison, the T/K ratio of $^{131}$I-RPS-001 does not reach 3 until nearly 96 h post injection. The T/K ratio of $^{131}$I-RPS-022 also increases rapidly, particularly at earlier time points (>1 at 12 h post injection), but this is driven more by rapid kidney clearance than by tumor uptake. The tumor-to-blood ratio of $^{131}$I-RPS-027 is lower than $^{131}$I-RPS-001 (FIG. 7B), predominantly reflecting enhanced albumin binding.

In comparison to $^{131}$I-MIP-1095, $^{131}$I-DCIBzL, and $^{211}$At-6, $^{131}$I-RPS-027 shows considerably lower kidney uptake at all time points from 1 h to 72 h post injection. See Hillier S, Rubino K, Maresca K, et al. [$^{131}$I]MIP-1466, a small molecule prostate-specific membrane antigen (PSMA) inhibitor for targeted radiotherapy of prostate cancer (PCa). *J Nucl Med.* 2012; 53(Suppl 1): 170, Chen Y, Foss C A, Byun Y, et al. Radiohalogenated prostate-specific membrane antigen (PSMA)-based ureas as imaging agents for prostate cancer. *J Med Chem.* 2008, 51:7933-7943, and Kiess A P, Minn I, Vaidyanathan G, et al. (2S)-2-(3-(l-Carboxy-5-(4-[211At]astatobenzamido)pentyl)ureido)-pentanedioic acid for PSMA-targeted α-particle radiopharmaceutical therapy. *J Nucl Med.* 2016; 57:1569-1575 (each of which is incorporated herein by reference) for $^{131}$I-MIP-1095, $^{131}$I-DCIBzL, and $^{211}$At-6, respectively.

The difference in uptake between $^{131}$I-MIP-1095 (alternately described herein as $^{131}$I-RPS-001) and $^{131}$I-RPS-027 at 24 h is 20-fold. In the context of the dosimetry reported for MIP-1095 in patients, the lower kidney uptake of $^{131}$I-RPS-027 projects to a significantly lower absorbed dose to the kidney, and a reduced risk of relevant nephrotoxicity at therapeutic doses or under a multiple treatment cycle regime. Moreover, the tumor-to-kidney ratio for $^{131}$I-RPS-027 is greater than 2 as soon as 18 h post injection, rises to 3 by 24 h and exceeds 7 by 72 h. This compares favorably to $^{211}$At-6, and a projection of the comparison between $^{131}$I-DCIBZL and $^{211}$At-6 to RPS-027 predicts that astatination will further increase the ratio. As such, the dose-limiting, irreversible nephrotoxicity of $^{211}$At-6 is expected to be resolved by $^{211}$At-RPS-027.

While certain embodiments have been illustrated and described, a person with ordinary-skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I (I)

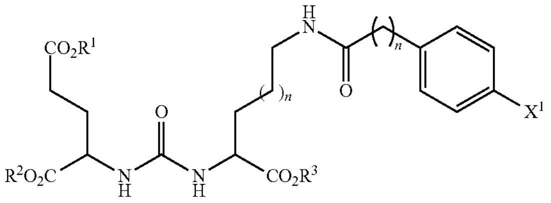

or a pharmaceutically acceptable salt thereof, wherein $X^1$ is $^{124}I$, $^{125}I$, $^{127}I$, $^{131}I$, $^{211}At$, or $Sn(R^4)_3$;

$R^1$, $R^2$, and $R^3$ are each independently H, methyl, benzyl, 4-methoxybenzyl, or tert-butyl;

$R^4$ is independently at each occurrence an alkyl group;

n is 1 or 2; and m is 0, 1, 2, or 3.

B. The compound of Paragraph A, wherein $R^1$, $R^2$, and $R^3$ are each independently H or tert-butyl, C. The compound of Paragraph A or Paragraph B, wherein $R^4$ is independently at each occurrence methyl, ethyl, propyl, propyl, or butyl.

D. The compound of any one of Paragraphs A-C, wherein when n is 2, then m is not 2, E. The compound of any one of Paragraphs A-D, wherein the compound of Formula I is a compound of Formula Ia (Ia)

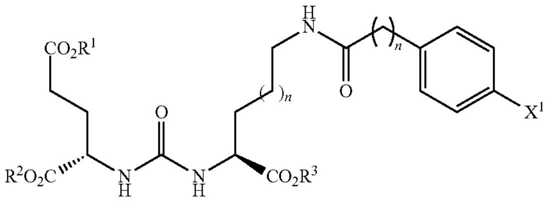

or a pharmaceutically acceptable salt thereof.

F. The compound of any one of Paragraphs A-E, wherein $X^1$ is $^{124}I$, $^{123}I$, $^{131}I$, or $^{211}At$.

G. A composition comprising a compound of any one of Paragraphs A-F and a pharmaceutically acceptable carrier.

H. A pharmaceutical composition for treating cancer expressing PSMA, the composition comprising an effective amount of the compound Paragraph F, wherein the effective amount is an amount effective for treating the cancer.

I. The pharmaceutical composition of Paragraph H, wherein the cancer is glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, or prostate cancer (such as castration resistant prostate cancer).

J. A method comprising administering a compound of Paragraph F to a subject suffering from a cancer expressing PSMA.

K. The method of Paragraph I, wherein the method comprises administering an effective amount of the compound to the subject.

L. The method of Paragraph J or Paragraph K, wherein the cancer is glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, or prostate cancer (such as castration resistant prostate cancer).

M. The method of any one of Paragraphs J-L, wherein administering the compound comprises parenteral administration, preferably intravenous administration.

N. A compound of Formula II (II)

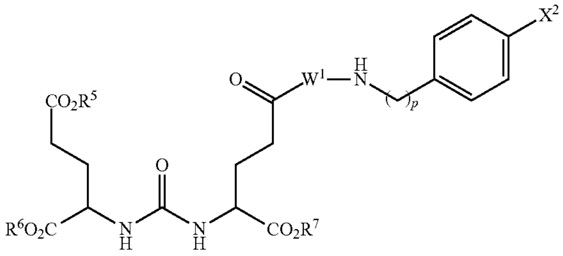

or a pharmaceutically acceptable salt thereof, wherein $X^2$ is $^{124}I$, $^{125}I$, $^{127}I$, $^{131}I$, $^{211}At$, or $Sn(R^8)_3$;

$R^5$, $R^6$, and $R^7$ are each independently H, methyl, benzyl, 4-methoxybenzyl, or tert-butyl;

$R^8$ is independently at each occurrence an alkyl group;

$W^1$ is a bond or —NH-alkylene-; and p is 0, 1, 2, or 3.

O. The compound of Paragraph N, wherein $R^5$, $R^6$, and $R^7$ are each independently H or tert-butyl.

P. The compound of Paragraph N or Paragraph O, wherein $R^8$ is independently at each occurrence methyl, ethyl, propyl, propyl, or butyl.

Q. The compound of any one of Paragraphs N-P, wherein the compound of Formula II is a compound of Formula Ha (IIa)

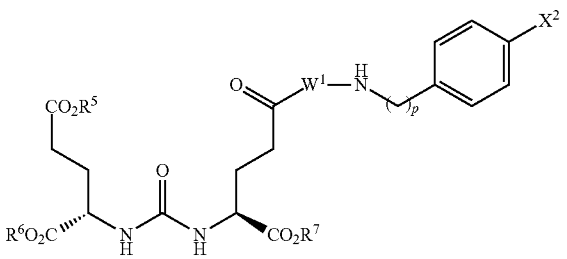

or a pharmaceutically acceptable salt, thereof.

R. The compound of any one of Paragraphs N-Q, wherein $X^1$ is $^{124}I$, $^{123}I$, $^{131}I$, or $^{211}At$.

S. A composition comprising a compound of any one of Paragraphs N-R and a pharmaceutically acceptable carrier.

T. A pharmaceutical composition for treating cancer expressing PSMA, the composition comprising an effective amount of the compound of Paragraph R and a pharmaceutically acceptable excipient, wherein the effective amount is an amount effective for treating the cancer, U. The pharmaceutical composition of Paragraph T, wherein the cancer is glioma, cervical carcinoma, vulvar carcinoma, endometrial carcinoma, primary ovarian carcinoma, metastatic ovarian carcinoma, non-small cell lung cancer, small ceil lung cancer, bladder cancer, colon cancer, primary, gastric adenocarcinoma, primary colorectal adenocarcinoma, renal cell carcinoma, or prostate cancer (such as castration resistant prostate cancer).

V. A method comprising administering a compound of Paragraph R to a subject suffering from cancer expressing PSMA.

W. The method of Paragraph V, wherein the method comprises administering an effective amount of the compound to the subject.

X. The method of Paragraph V or Paragraph W, wherein the cancer is glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, or prostate cancer (such as castration resistant prostate cancer).

Y. The method of any one of Paragraphs V-X, wherein administering the compound comprises parenteral administration, preferably intravenous administration, Z. A method of enhancing uptake of a therapeutic agent to a tumor presenting prostate specific membrane antigen ("PSMA"), the method comprising administering a first therapeutic agent comprising a PMSA targeting moiety and a human serum albumin binding moiety to a subject with one or more cancer tumors, where the human serum albumin binding moiety includes a radionuclide;

detecting distribution of the first therapeutic agent in the subject; and modifying the human serum albumin binding moiety of the first therapeutic agent to provide a second therapeutic agent.

AA. The method of Paragraph Z, wherein the PMSA-targeting moiety comprises a glutamate-urea-glutamate moiety or a glutamate-urea-lysine moiety.

AB. The method of Paragraph Z or Paragraph AA, wherein the cancer is glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, or prostate cancer (such as castration resistant prostate cancer).

AC. The method of any one of Paragraphs Z-AB, wherein the human serum albumin binding moiety includes a $^{124}$I-substituted, a $^{125}$I-substituted, a $^{131}$I-substituted, or $^{211}$At-substituted phenyl moiety.

AD. The method of any one of Paragraphs Z-AC, wherein the human serum albumin binding moiety includes a 4-($^{124}$I)-substituted, a 4-($^{125}$I)-substituted, a 4-($^{131}$I)-substituted, or a 4-($^{211}$At)-substituted phenyl moiety.

AE. The method of any one of Paragraphs Z-AD, wherein modifying the first therapeutic agent comprises lengthening or shortening a hydrocarbon chain of the human serum albumin binding moiety.

AF. The method of any one of Paragraphs Z-AE, wherein administering the first therapeutic agent comprises parenteral administration.

AG. The method of any one of Paragraphs Z-AF, wherein the method further comprises administering the second therapeutic agent to a subject with one or more cancer tumors;

detecting distribution of the second therapeutic agent in the subject.

AH. The method of Paragraph AG, wherein the second therapeutic agent exhibits higher tumor uptake in comparison with non-tumor tissues of the subject than the first therapeutic agent.

AI. The method of any one of Paragraphs Z-AH, wherein the modifying the first therapeutic agent comprises conjugating a polyalkane glycol, polyethylene amine (PEI), polyglycine, carbohydrate polymer, amino acid polymer, polyvinyl pyrolidone, a fatty acid, a fatty acid ester group, or a combination of any two or more thereof to the human serum albumin binding moiety.

AJ. The method of Paragraph AI, wherein the conjugating step comprises inserting a polyalkane glycol, polyethylene amine (PEI), polyglycine, carbohydrate polymer, amino acid polymer, polyvinyl pyrolidone, a fatty acid, a fatty acid ester group, or a combination of any two or more thereof between the PSMA-targeting moiety and the human serum albumin binding moiety.

AK. The method of Paragraph AI or Paragraph AI, wherein the conjugating step comprises conjugating a polyalkane glycol, polyethylene amine (PEI), polyglycine, carbohydrate polymer, amino acid polymer, polyvinyl pyrolidone, a fatty acid, a fatty acid ester group, or a combination of any two or more thereof at a position on the human serum albumin binding moiety that is distal to the PSMA-targeting moiety.

Other embodiments are set forth in the following claims, along with the full scope of equivalents to which such claims are entitled.

What is claimed is:

1. A compound that is

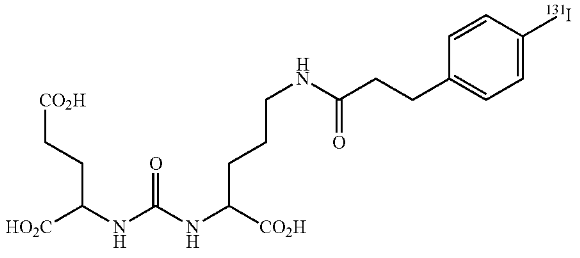 [SMILES: O=C(O)CCC(NC(=O)NC(CCCNC(=O)CCc1ccc([131I])cc1)C(=O)O)C(=O)O]

or a pharmaceutically acceptable salt thereof.

2. A compound that is

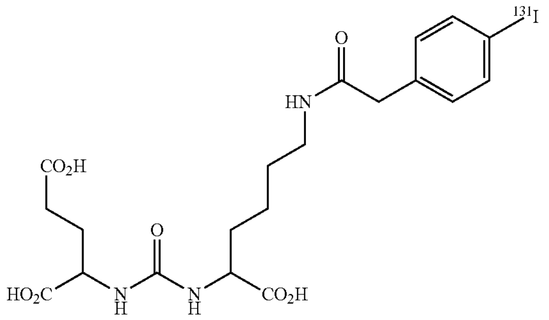 [SMILES: O=C(O)CCC(NC(=O)NC(CCCCNC(=O)Cc1ccc([131I])cc1)C(=O)O)C(=O)O]

or a pharmaceutically acceptable salt thereof.

* * * * *